(12) United States Patent
Stutman et al.

(10) Patent No.: US 9,823,202 B2
(45) Date of Patent: *Nov. 21, 2017

(54) DIFFERENTIAL PHASE CONTRAST X-RAY IMAGING SYSTEM AND COMPONENTS

(71) Applicant: The Johns Hopkins University, Baltimore, MD (US)

(72) Inventors: Daniel Stutman, Cockeysville, MD (US); Michael Finkenthal, Columbia, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/370,280

(22) Filed: Dec. 6, 2016

(65) Prior Publication Data

US 2017/0146466 A1    May 25, 2017

Related U.S. Application Data

(60) Division of application No. 14/280,272, filed on May 16, 2014, now Pat. No. 9,557,279, which is a continuation of application No. 13/493,392, filed on Jun. 11, 2012, now Pat. No. 8,767,915.

(60) Provisional application No. 61/513,175, filed on Jul. 29, 2011, provisional application No. 61/620,140, filed on Apr. 4, 2012.

(51) Int. Cl.
*A61B 6/00* (2006.01)
*G01N 23/04* (2006.01)
*G01N 23/20* (2006.01)
*G21K 1/06* (2006.01)
(Continued)

(52) U.S. Cl.
CPC ............... *G01N 23/04* (2013.01); *A61B 6/40* (2013.01); *A61B 6/4035* (2013.01); *A61B 6/4042* (2013.01); *A61B 6/4291* (2013.01); *A61B 6/482* (2013.01); *A61B 6/484* (2013.01); *A61B 6/5235* (2013.01); *A61B 6/583* (2013.01); *G01N 23/087* (2013.01); *G01N 23/20075* (2013.01); *G21K 1/067* (2013.01); *A61B 6/4241* (2013.01); *A61B 6/483* (2013.01); *A61B 6/505* (2013.01);
(Continued)

(58) Field of Classification Search
CPC ..................................................... G21K 1/067
See application file for complete search history.

(56) References Cited

U.S. PATENT DOCUMENTS 4,798,446 A    1/1989    Hettrick
5,812,629 A    9/1998    Clauser
(Continued)

FOREIGN PATENT DOCUMENTS

JP    H06109671 A    4/1994
JP    2008-545981 A    12/2008

OTHER PUBLICATIONS

Arfelli et al., Phys. Med. Biol. 55 1643 (2010).
(Continued)

*Primary Examiner* — Dani Fox
(74) *Attorney, Agent, or Firm* — Venable LLP; Henry J. Daley; Laura G. Remus

(57) ABSTRACT

A differential phase contrast X-ray imaging system includes an X-ray illumination system, a beam splitter arranged in an optical path of the X-ray illumination system, and a detection system arranged in an optical path to detect X-rays after passing through the beam splitter.

7 Claims, 19 Drawing Sheets

(51) Int. Cl.
*G01N 23/087* (2006.01)
*H05G 2/00* (2006.01)

(52) U.S. Cl.
CPC . *G01N 2223/206* (2013.01); *G21K 2207/005* (2013.01); *H05G 2/001* (2013.01)

(56) References Cited

U.S. PATENT DOCUMENTS

| | | | |
|---|---|---|---|
| 6,804,324 B2 | 10/2004 | Martynov et al. | |
| 7,889,838 B2 | 2/2011 | David et al. | |
| 8,850,640 B2 | 10/2014 | Buettner | |
| 2006/0002512 A1* | 1/2006 | Cho | A61B 6/032 378/84 |
| 2010/0091936 A1 | 4/2010 | David et al. | |
| 2010/0272235 A1 | 10/2010 | Takahashi | |

OTHER PUBLICATIONS

Bech et al., "Hard X-ray phase-contrast imaging with the Compact Light Source based on inverse Compton X-rays," J. Synchrotron Rad. 16, 43 (2009).
Bech et al., "Soft-tissue phase-contrast tomography with an X-ray tube source," Phys. Med. Biol. 54 2747 (2009).
Brey et al., Tissue Eng. Part C Methods. 16, 1597 (2010).
Chapman, et al. Phys. Med. Biol. 42 2015 (1997).
Coan et al., "Analyzer-based imaging technique in tomography of cartilage and metal implants: A study at the ESRF," European Journal of Radiology 68, S41 (2008).
Cornaby et al., J. Synchrotron Rad. 15, 371 (2008).
David et al., "Fabrication of diffraction gratings for hard X-ray phase contrast imaging," Microelectronic Engineering 84, 1172 (2007).
Donath et al. J. Appl. Phys. 106 054703(2009).
Donath et al. Investigative Radiology 45, 445 (2010).
Donath et al., "Phase-contrast imaging and tomography at 60 keV using a conventional X-ray tube source," Rev. Sci. Instrum. 80, 053701 (2009).
Engelhardt et al. Journal of Microscopy 232, 145 (2008).
Hussein et al. Phys. Med. Biol. 54 1533 (2009).
Iida et al. Nucl. Instrum. Meth. Phys. Res. A235, 597 (1985).
Joensen et al. Proc. SPIE vol. 2011 Multilayer and Grazing Incidence X-Ray/EUV Optics II, 360 (1994).
Kashyap et al., "Laboratory-based X-ray phase-contrast imaging technique for material and medical science applications," Applied Radiation and Isotopes 66, 1083 (2008).
Keyriläinen et al. Acta Radiologica 8 866(2010).
Koch et al., "Refraction-enhanced X-ray radiography for inertial confinement fusion and laser-produced plasma applications," J. Appl. Phys. 105, 113112 (2009).
Lawaczeck et al., Investigative Radiology 40, 33 (2005).
Lewis, "Medical phase contrast X-ray imaging: current status and future prospects," Phys. Med. Biol. 49, 3573 (2004).
Li et al., "Phase-sensitive X-ray imaging of synovial joints", Osteoarthritis and Cartilage 17, 1193 (2009).
Mayo et al., "X-ray phase-contrast micro-tomography and image analysis of wood microstructure," Journal of Physics: Conference Series 186, 012105 (2009).
Momose et al., "Phase Tomography by X-ray Talbot Interferometry for Biological Imaging," Japanese Journal of Applied Physics 45, 5254 (2006).
Muehleman et al., "Diffraction-enhanced imaging of musculoskeletal tissues using a conventional X-ray tube," Acad. Radiol. 16, 918 (2009).
Muehleman et al., "Multiple-image radiography for human soft tissue," J. Anat. 208, 115 (2006).
Park et al., Physics of Plasmas 15, 07270 (2008).
Park et al., Proc. SPIE 7258 Medical Imaging 2009: Physics of Medical Imaging, 72583L (2009).
Pfeiffer et al., "Phase retrieval and differential phase-contrast imaging with low-brilliance X-ray sources," Nature Physics 2, 258 (2006).
Pfeiffer et al., "Hard-X-ray dark-field imaging using a grating interferometer," Nature Materials 7, 134 (2008).
Rack et al., Proc. SPIE vol. 7802, Advances in X-Ray/EUV Optics and Components V, 78020M-1 (2010).
Ress et al., Rev. Sci. Instrum. 66, 579 (1995).
Reznikova et al., "Soft X-ray lithography of high aspect ratio SU8 submicron structures," Microsyst. Technol. 14, 1683 (2008).
Sanchez et al., "XOP: recent developments, in Crystal and Multilayer Optics," Proc. SPIE 3448, 340 (1998).
Schuster et al., Proc. SPIE vol. 3767 EUV, X-Ray, and Neutron Optics and Sources, 183 (1999).
Shimao et al., European Journal of Radiology 68 S27 (2008).
Stevenson et al., Nuclear Instruments and Methods in Physics Research B 199 427 (2003).
Strobl et al., "Neutron Dark-Field Tomography," Phys. Rev. Lett. 101, 123902 (2008).
Stutman et al., Rev. Sci. Instrum. 81, 10E504 (2010).
Stutman et al., Applied Optics 49, 4677 (2010).
Stutman et al., Phys. Med. Biol. 56, (5697) 2011.
Suhonen et al., "Refraction and scattering of X-rays in analyzer based imaging," J. Synchrotron Rad. 14, 512 (2007).
Testorf, et al., Opt. Commun. 129, 167-172 (1996).
Tommasini, LLNL Report, LLNL-TR-429373, 2010.
Weitkamp, "XWFP: An X-ray wavefront propagation software package for the IDL computer language," Proc. SPIE 5536, 181-189 (2004).
Weitkamp et al., "Tomography with grating interferometers at low-brilliance sources," Proc. SPIE 6318, 6318 (2006).
Wen et al., Optics Express 19, 25093 (2011).
Woodard et al., The British Journal of Radiology 59, 1209 (1986).
Yuasa et al., "Highly sensitive detection of the soft tissues based on refraction contrast by in-plane diffraction-enhanced imaging CT," Nuclear Instruments and Methods in Physics Research A 591, 546 (2008).
Zhou et al., "Development of phase-contrast X-ray imaging techniques and potential medical applications," Physica Medica 24, 129 (2008).
Office Action issued in Japanese Patent Application No. 2014-522824 dated Aug. 26, 2014.
Office Action issued in European Patent Application No. 12819196.2 dated Nov. 24, 2014.
Kemble et al., "Grazing angle Mach-Zehnder interferometer using reflective phase gratings and a polychromatic, un-collimated light source," Optics Express, vol. 18, Dec. 2010, pp. 27481-27492.

* cited by examiner

DIFFERENTIAL PHASE CONTRAST X-RAY IMAGING SYSTEM AND COMPONENTS

CROSS-REFERENCE OF RELATED APPLICATION

This application is a divisional of U.S. application Ser. No. 14/280,272, filed May 16, 2014, which is a continuation of U.S. application Ser. No. 13/493,392, filed Jun. 11, 2012 which claims priority to U.S. Provisional Application No. 61/513,175, filed Jul. 29, 2011, and U.S. Provisional Application No. 61/620,140, filed Apr. 4, 2012, the entire contents of which are hereby incorporated by reference.

This invention was made with Government support of Grant No. DE-FG02-99ER54523, awarded by the Department of Energy; and Grant No. 1R21EB012777-01A1, awarded by the Department of Health and Human Services, The National Institutes of Health (NIH). The U.S. Government has certain rights in this invention.

BACKGROUND

1. Field of Invention

The field of the currently claimed embodiments of this invention relates to X-ray systems, and more particularly to differential phase contrast X-ray imaging systems and X-ray illumination systems.

2. Discussion of Related Art

X-ray differential phase-contrast (DPC) imaging relies on the refraction of the X-rays passing through an object. Since for hard X-rays the refraction angles are in the μ-radian range, the basic technique used for DPC imaging is to angularly filter with μ-radian resolution the transmitted X-ray beam, thus converting the angular beam deviations from refraction into intensity changes on a conventional detector. The angular filtering is done using X-ray optics such as crystals or gratings (see [1] for a recent review).

A fundamental advantage of DPC imaging is that it is sensitive to density gradients in the measured object rather than to its bulk X-ray absorption. In medical imaging for instance refraction has a contrast enhancing effect at tissue boundaries, which enables the detection of soft tissues which are otherwise invisible in conventional X-ray imaging. The ultra-small angle scattering occurring in micro-structured soft tissue such as cartilage, tendon, ligament or muscle has also a volume contrast enhancing effect [1-5]. Another benefit of DPC for medical imaging is that it can improve contrast and resolution at similar or lower dose than in conventional X-ray imaging. This is possible because DPC uses X-rays that are not absorbed by the body and because the soft tissue refraction coefficients decrease with X-ray energy much slower than the absorption ones. In particular, by using for DPC a spectrum with mean energy in the 50-80 keV range approximately, the soft tissue dose is minimized while refraction strongly dominates over absorption [1, 6].

X-ray phase-contrast is also of interest for imaging and non-destructive characterization in material sciences, in particular as concerns low-Z materials. The structure and defects of materials ranging from polymers, to fiber composites, to wood, and to engineered bio-materials can be probed on the micrometer scale using X-ray phase-contrast [7-9]. Some of the techniques used for X-ray phase-contrast can also be applied with neutrons [10]. Recently X-ray phase-contrast has gained attention in fusion energy research, where the capability of refraction based imaging to measure the density gradients in an object can be used for the diagnostic of high density plasmas in inertial confinement fusion (ICF) and other high energy density physics (HEDP) experiments [11].

Until recently, research on X-ray DPC imaging has been done mostly at synchrotrons, using crystal optics; the high intensity of the synchrotron compensates for the low efficiency (less than a hundredth of a %) of the crystal optics [1, 12]. Although there are efforts to develop table-top synchrotrons [13], or to use narrow $K_\alpha$ lines from conventional tubes [14], the crystal method has not yet entered the domain of practical applications. It is thus of interest to develop more efficient DPC methods and optics, that can work with conventional medical or industrial X-ray tubes.

A DPC method that can work with conventional X-ray sources is the Talbot-Lau shearing interferometry, in which micro-periodic optics such as gratings are used to angularly filter the refracted X-rays with μ-radian resolution [15-17]. The Talbot interferometer includes first a 'beam-splitter' (typically a π-shift phase grating), which divides (or 'shears') through the Talbot effect the incoming beam into few μ-radian wide beamlets. The Talbot effect consists in a 'replication' of the grating pattern by the wave intensity, at periodic distances along the beam, called Talbot distances, $d_T = k/\eta^2 \cdot g^2/(2\lambda)$, with λ the X-ray wavelength, g the grating period, k=1, 2, . . . the order of the pattern, and η=1 for a π/2 phase shifting grating or for an absorption grating, and η=2 for a π phase grating [18]. The beam-splitter thus creates at the 'Talbot distance' a micro-periodic fringe pattern, which changes shape (shifts) with respect to the unperturbed pattern when a refractive object is introduced in the beam. The differential phase-contrast imaging consists thus in measuring the changes in the fringe pattern induced by the object, with respect to the pattern without the object. To achieve μ-radian angular sensitivity at hard X-ray wavelengths, the period g must be in the μm range, resulting in a Talbot distance of a few tens of cm.

The fringe pattern can in principle be directly measured using a microscopic pixel detector [17]. This is however quite inefficient. For most practical applications, the fringe pattern changes are converted into intensity changes on a macroscopic pixel detector by introducing an 'analyzer' absorption grating placed behind the beam-splitter and having the period of the Talbot pattern. Lastly, for such an interferometer to function with an extended spot X-ray tube, a 'source' absorption grating is placed in front of the source, thus dividing it into an array of quasi-coherent line sources [16-18].

The gratings are made by micro-lithography in thin Si wafers or photoresist [19, 20]. The absorption gratings are difficult to fabricate; they are typically made by filling with gold the gaps in regular transmission gratings. The 'grating shearing method' described above has demonstrated performance similar to the crystal method at energies below a few tens of keV [21].

This method is however less useful at energies above a few tens of keV. The reason is that it is difficult to fabricate micron-period absorption gratings with the thickness required to block higher energy X-rays. This is illustrated in FIG. 1 with a plot of the Au thickness needed for 95% absorption, as a function of the photon energy. As seen, several hundred μm depth gratings would be needed in the range of interest for clinical DPC imaging. Depending on the grating period, the present technological limit is however around 50-100 μm [19, 20, 22]. This limits the contrast of the grating shearing method for high energy X-rays, as illustrated in FIG. 1 by the fringe contrast computed for an interferometer having 30 μm thick, 4 μm period Au analyzer grating (throughout this specification we used for X-ray phase-contrast and optics calculations the XWFP wave propagation code [23] and the XOP optics package [24]).

A new type of optics is therefore needed to enable efficient DPC imaging at X-ray energies above a few tens of keV.

BACKGROUND REFERENCES

1. Shu-Ang Zhou and Anders Brahme, "Development of phase-contrast X-ray imaging techniques and potential medical applications", Physica Medica 24, 129 (2008).
2. Carol Muehleman, Jun Li, Zhong Zhong, Jovan G. Brankov and Miles N. Wernick, "Multiple-image radiography for human soft tissue", J. Anat. 208, 115 (2006)
3. Tetsuya Yuasa, Eiko Hashimoto, Anton Maksimenko, Hiroshi Sugiyama, Yoshinori Arai, Daisuke Shimao, Shu Ichihara, Masami Ando, "Highly sensitive detection of the soft tissues based on refraction contrast by in-plane diffraction-enhanced imaging CT", Nuclear Instruments and Methods in Physics Research A 591, 546 (2008)
4. J. Li, Z. Zhong, D. Connor, J. Mollenhauer and C. Muehleman, "Phase-sensitive X-ray imaging of synovial joints", Osteoarthritis and Cartilage 17, 1193 (2009)
5. Paola Coan, Juergen Mollenhauer, Andreas Wagner, Carol Muehleman, Alberto Bravin, "Analyzer-based imaging technique in tomography of cartilage and metal implants: A study at the ESRF", European Journal of Radiology 68, S41 (2008)
6. R A Lewis, "Medical phase contrast X-ray imaging: current status and future prospects", Phys. Med. Biol. 49, 3573 (2004)
7. F. Pfeiffer, M. Bech, O. Bunk, P. Kraft, E. F. Eikenberry, Ch. Bronnimann, C. Grunzweig and C. David, "Hard-X-ray dark-field imaging using a grating interferometer", Nature Materials 7, 134 (2008)
8. Yogesh S. Kashyap, P. S. Yadav, Tushar Roy, P. S. Sarkar, M. Shukla, Amar Sinha, "Laboratory-based X-ray phase-contrast imaging technique for material and medical science applications", Applied Radiation and Isotopes 66, 1083 (2008)
9. Sheridan Mayo, Robert Evans, Fiona Chen and Ryan Lagerstrom, "X-ray phase-contrast micro-tomography and image analysis of wood microstructure", Journal of Physics: Conference Series 186, 012105 (2009)
10. M. Strobl, C. Grünzweig, A. Hilger, I. Manke, N. Kardjilov, C. David, and F. Pfeiffer, "Neutron Dark-Field Tomography", Phys. Rev. Lett. 101, 123902 (2008)
11. Jeffrey A. Koch, Otto L. Landen, Bernard J. Kozioziemski, Nobuhiko Izumi, Eduard L. Dewald, Jay D. Salmonson, and Bruce A. Hammel, "Refraction-enhanced X-ray radiography for inertial confinement fusion and laser-produced plasma applications", J. Appl. Phys. 105, 113112 (2009)
12. Heikki Suhonen, Manuel Fernandez, Alberto Bravin, Jani Keyrilainen and Pekka Suorttia, "Refraction and scattering of X-rays in analyzer based imaging", J. Synchrotron Rad. 14, 512 (2007)
13. Martin Bech, Oliver Bunk, Christian David, Ronald Ruth, Jeff Rifkin, Rod Loewen, Robert Feidenhans and Franz Pfeiffer, "Hard X-ray phase-contrast imaging with the Compact Light Source based on inverse Compton X-rays", J. Synchrotron Rad. 16, 43 (2009)
14. Muehleman C, Li J, Connor D, Parham C, Pisano E, Zhong Z., "Diffraction-enhanced imaging of musculoskeletal tissues using a conventional X-ray tube", Acad. Radiol. 16, 918 (2009)
15. J. F. Clauser, "Ultrahigh resolution interferometric X-ray imaging," U.S. Pat. No. 5,812,629 (1998)
16. Pfeiffer, F., Weitkamp, T., Bunk, O., David, C., "Phase retrieval and differential phase-contrast imaging with low-brilliance X-ray sources", Nature Physics 2, 258 (2006)
17. Atsushi Momose, Wataru Yashiro, Yoshihiro Takeda, Yoshio Suzuki and Tadashi Hattori, "Phase Tomography by X-ray Talbot Interferometry for Biological Imaging", Japanese Journal of Applied Physics 45, 5254 (2006)
18. Timm Weitkamp, Christian David, Christian Kottler, Oliver Bunk, and Franz Pfeiffer, "Tomography with grating interferometers at low-brilliance sources", Proc. SPIE 6318, 6318 (2006)
19. C. David, J. Bruder, T. Rohbeck, C. Grunzweig, C. Kottler, A. Diaz, O. Bunk, F. Pfeiffer, "Fabrication of diffraction gratings for hard X-ray phase contrast imaging" Microelectronic Engineering 84, 1172 (2007)
20. Elena Reznikova, Juergen Mohr, Martin Boerner, Vladimir Nazmov, Peter-Juergen Jakobs, "Soft X-ray lithography of high aspect ratio SU8 submicron structures", Microsyst. Technol. 14, 1683 (2008)
21. Martin Bech, Torben H Jensen, Robert Feidenhans, Oliver Bunk, Christian David and Franz Pfeiffer, "Soft-tissue phase-contrast tomography with an X-ray tube source", Phys. Med. Biol. 54 2747 (2009)
22. Tilman Donath, Franz Pfeiffer, Oliver Bunk, Waldemar Groot, et al., "Phase-contrast imaging and tomography at 60 keV using a conventional X-ray tube source", Rev. Sci. Instrum. 80, 053701 (2009)
23. Timm Weitkamp, "XWFP: An X-ray wavefront propagation software package for the IDL computer language", Proc. SPIE 5536, 181-189 (2004)
24. M. Sanchez del Rio and R. J. Dejus, "XOP: recent developments, in Crystal and Multilayer Optics", Proc. SPIE 3448, 340 (1998)

SUMMARY

A differential phase contrast X-ray imaging system according to an embodiment of the current invention includes an X-ray illumination system, a beam splitter arranged in an optical path of the X-ray illumination system, and a detection system arranged in an optical path to detect X-rays after passing through the beam splitter. The detection system includes an X-ray detection component. The beam splitter includes a splitter grating arranged to intercept an incident X-ray beam and provide an interference pattern of X-rays. The detection system includes an analyzer grating arranged to intercept and block at least portions of the interference pattern of X-rays prior to reaching the X-ray detection component. The analyzer grating has a longitudinal dimension, a lateral dimension that is orthogonal to the longitudinal dimension and a transverse dimension that is orthogonal to the longitudinal and lateral dimensions. The analyzer grating includes a pattern of optically dense regions each having a longest dimension along the longitudinal dimension that are spaced substantially parallel to each other in the lateral dimension such that there are optically rare regions between adjacent optically dense regions. Each optically dense region has a depth in the transverse dimension that is smaller than a length in the longitudinal dimension. The analyzer grating is arranged with the longitudinal dimension at a shallow angle relative to incident X-rays and the shallow angle is less than 30 degrees.

An X-ray illumination system according to an embodiment of the current invention includes a poly-energetic X-ray source and a band-pass filter arranged in an optical path of X-rays from the poly-energetic X-ray source. The band-pass filter allows X-rays within a band of energies to pass more strongly than X-rays outside the band of energies.

BRIEF DESCRIPTION OF THE DRAWINGS

Further objectives and advantages will become apparent from a consideration of the description, drawings, and examples.

DETAILED DESCRIPTION

Figure 1:
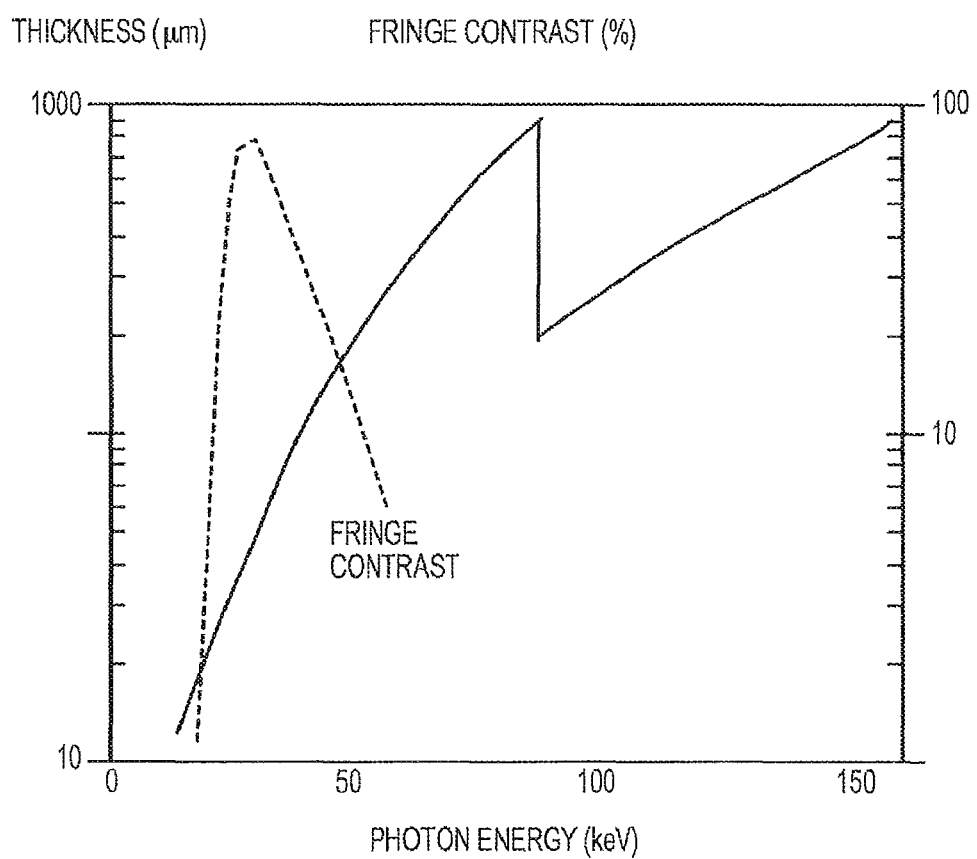
FIG. 1 shows gold thickness needed for 95% absorption, as a function of X-ray energy. Also shown the fringe contrast for a grating interferometer having 30 μm thick, 4 μm period Au analyzer. At energies of clinical interest the analyzer becomes transparent to X-rays, drastically reducing the interferometer contrast.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Some embodiments of the current invention can use commercially available micro-periodic gratings tilted at glancing incidence (incidence angles α in the range from a few degrees to a few tens of degrees), to make Talbot-Lau differential phase-contrast (DPC) interferometers up to very high X-ray energy (100 keV and higher). Some embodiments of the current invention may also include grazing incidence mirrors in conjunction with the tilted gratings that help to produce a quasi-monochromatic X-ray spectrum and/or to improve the coherence of the radiation incident on the gratings.

Some applications, according to some embodiments of the current invention, can include medical X-ray imaging where refraction and ultra-small-angle scatter (USAXS) have been shown to strongly enhance the visibility of soft tissues, such cartilage, tendon, blood vessel walls, brain tissue, micro calcifications, and tumors. Some embodiments of the current invention can work with high energy X-rays and with high power, extended spot medical X-ray tubes, thus enabling X-ray phase-contrast imaging of tissues deep in the human body. Examples of possible medical applications are 'X-ray biopsy' systems that may enable early cancer detection for organs deep in the body, such as the prostate, lung, pancreas, or brain.

In addition, other applications of some embodiments of the current invention can be used in the field of engineered tissues, material sciences and materials based on nanostructures, industrial non-destructive testing (NDT), and security screening and energy research, for example. In NDT for instance, phase-contrast imaging with X-rays around 100 keV could enable improved detection of cracks and microstructural fatigue damage in critical components such as airplane wings and fuselage. However, the general concepts of the current invention are not limited to these particular examples.

The main imaging modalities for soft tissues are MRI, ultrasound, and X-rays. However, while MRI and ultrasound provide good soft tissue contrast, their spatial resolution is limited. Conventional (attenuation based) X-ray imaging on the other hand has good spatial resolution, but poor soft tissue contrast.

In recent years a new X-ray imaging modality called differential phase-contrast (DPC) and based on X-ray refraction and ultra-small angle scatter has been explored that offers both good soft tissue contrast and high spatial resolution. These capabilities arise from the sensitivity of DPC to small-scale density gradients in the object rather than to its bulk absorption. This enhances the contrast for tissue boundaries and for micro-structured tissues such as cartilage, tendon, ligament or muscle. In addition, recent studies show that DPC can provide sensitive detection of tumors in a variety of organs, from the breast, to the liver and to the lung. There is thus a rapidly growing spectrum of possible medical applications of X-ray DPC [1]. In addition, there could be many novel applications of X-ray phase-contrast in non-destructive testing and material sciences.

DPC imaging works by using X-ray optics to angularly filter the refracted component in the transmitted radiation. Recently a very efficient DPC method was developed that enables the use of conventional X-ray tubes. The method is based on the Talbot-Lau interferometer setup in which micro-periodic absorption and transmission gratings are used to angularly filter the refracted X-rays [2,3].

Due to technological limits in the fabrication of thick micro-periodic gratings [4,5], the conventional Talbot-Lau interferometer using gratings at normal incidence has insufficient fringe contrast or visibility at X-ray energies above a few tens of keV [2-4]. X-rays above a few tens of KeV are however needed to penetrate large body parts. The same limitation occurs in industrial or material research applications of DPC imaging.

Some embodiments of the current invention are directed to a new type of X-ray imaging systems based on Talbot-Lau interferometers having glancing incidence micro-periodic gratings, or combinations of glancing incidence gratings and mirrors. These systems can enable high resolution DPC imaging with X-rays up to 100 keV or higher and using conventional, extended spot X-ray tubes. The systems described according to some embodiments of the current invention also have sufficiently large 2-D fields of view (order of 2×7 cm for a single interferometer) to enable most practical applications.

Some embodiments of the current invention can be used in combination with and/or further develop concepts described by the current inventors in MICRO-PERIODIC MIRROR BASED SYSTEMS FOR PHASE-CONTRAST IMAGING WITH HARD X-RAYS [7]. This previously reported system can provide DPC imaging at high energy, but one distinction is that the field of view is limited to a few hundred μm in one dimension.

Figure 2A:
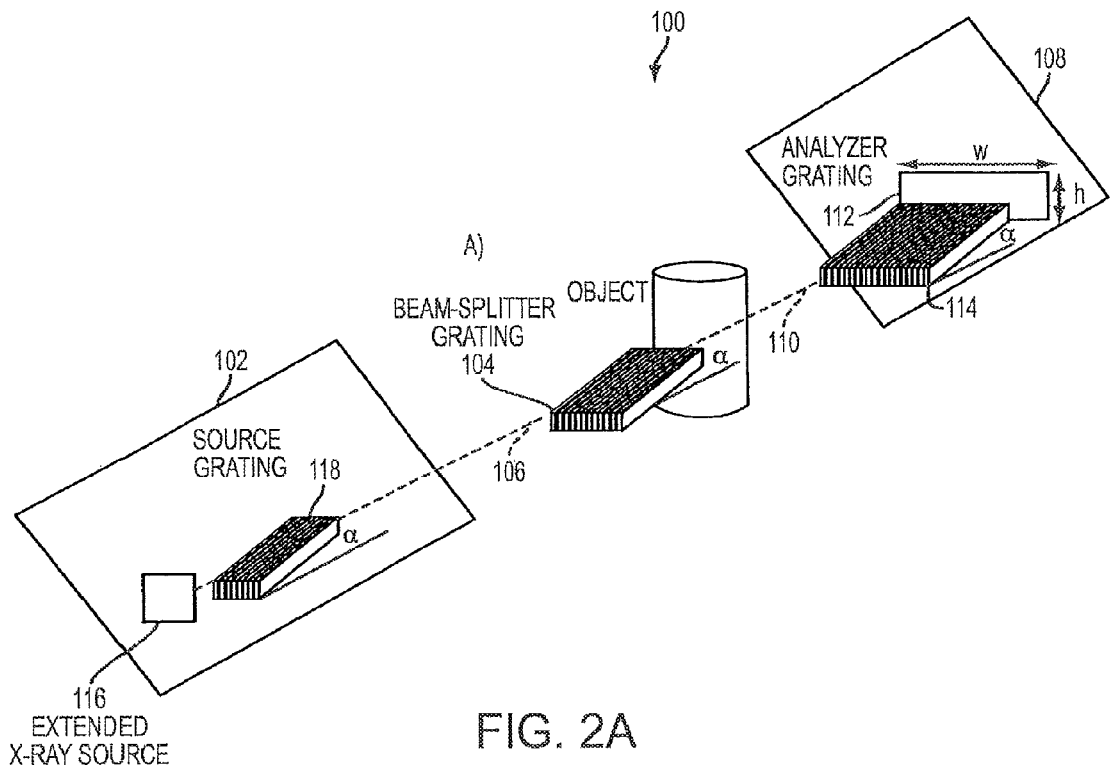
FIG. 2A is a schematic illustration of a differential phase contrast X-ray imaging system according to an embodiment of the current invention.

FIG. 2A provides a schematic illustration of a differential phase contrast X-ray imaging system 100 according to an embodiment of the current invention. The differential phase contrast X-ray imaging system 100 includes an X-ray illumination system 102, a beam splitter 104 arranged in an optical path 106 of the X-ray illumination system 102, and a detection system 108 arranged in an optical path 110 to detect X-rays after passing through the beam splitter 104. The detection system 108 includes an X-ray detection component 112. The beam splitter 104 includes a splitter grating, as is shown in the embodiment of FIG. 2A, arranged to intercept an incident X-ray beam and provide an interference pattern of X-rays.

The detection system 108 also includes an analyzer grating 114 arranged to intercept and block at least portions of the interference pattern of X-rays prior to reaching the X-ray detection component 112. The analyzer grating 114 has a longitudinal dimension, a lateral dimension that is orthogonal to the longitudinal dimension, and a transverse dimension that is orthogonal to the longitudinal and lateral dimensions. The analyzer grating 114 has a pattern of optically dense regions, each having a longest dimension along the longitudinal dimension and spaced substantially parallel to each other in the lateral dimension such that there are optically rare regions between adjacent optically dense regions. Each optically dense region has a depth in the transverse dimension that is smaller than a length in the longitudinal dimension. The analyzer grating 114 is arranged with the longitudinal dimension at a shallow angle α relative to incident X-rays such that the shallow angle α is less than 30 degrees. As is illustrated in the embodiment of FIG. 2A, the longitudinal dimension of the analyzer grating 114 is oriented substantially along the optical path 110 (which can be the optical axis, for example), except tilted at the shallow angle α. (This will also be referred to as a glancing angle.)

In an embodiment of the current invention, each optically dense region has a depth in the transverse dimension that is smaller than a length in the longitudinal dimension by at least a factor of two. In an embodiment, each optically dense region has a depth in the transverse dimension that is smaller than a length in the longitudinal dimension by at least a factor of ten. In a further embodiment, each optically dense region has a depth in the transverse dimension that is smaller than a length in the longitudinal dimension by at least a factor of one hundred.

Figure 4:
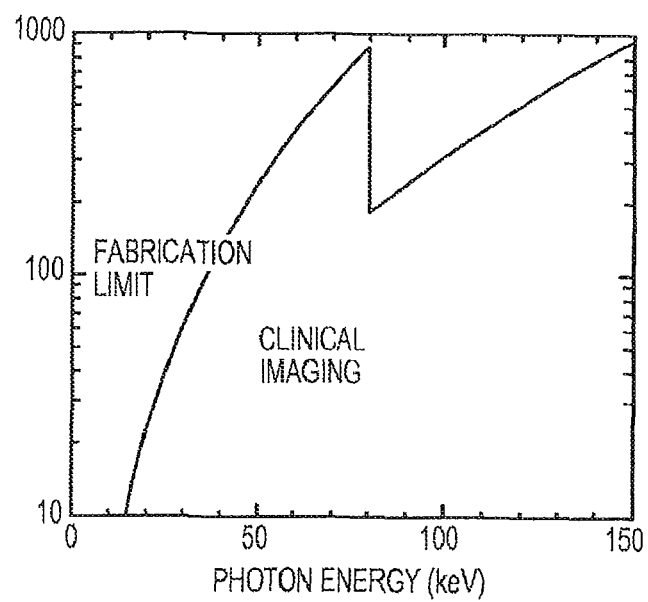
FIG. 4 is a plot of Au thickness needed for 95% absorption, as a function of X-ray energy.

In an embodiment of the current invention, the shallow angle α is less than 25 degrees and greater than 5 degrees. In another embodiment, the shallow angle α is less than 15 degrees and greater than 3 degrees. An embodiment of the current invention is directed to medical applications. Since it is difficult to produce few-micron period gratings with more than ~100 μm Au absorber thickness, inclining the gratings at an angle in the 5-25° range makes for 200-1000 μm effective Au thickness. As is shown in FIG. 4, this thickness enables >90% X-ray absorption (and thus high interferometer contrast) over the ~40 keV-110 keV energy range, of interest for medical phase-contrast imaging deep in the body. Another embodiment is directed to industrial or non-destructive testing (NDT) applications. Using glancing angles in the 3-15° range, the effective Au thickness is in the 400-2000 μm range, which makes for good X-ray absorption and interferometer contrast in the ~100 keV-250 keV energy range of interest for industrial NDT applications.

In an embodiment of the current invention, the splitter grating 104 is a reflection grating (not shown in FIG. 2A). A reflection grating such as described in Ref. [7], which is incorporated herein by reference, can be used according to some embodiments of the current invention. In an embodiment of the current invention, the splitter grating 104 is a transmission grating, as is illustrated schematically in FIG. 2A. According to an embodiment of the current invention in which the splitter grating 104 is a transmission grating, similar to analyzer grating 114, such an embodiment of the analyzer grating has a longitudinal dimension, a lateral dimension that is orthogonal to the longitudinal dimension, and a transverse dimension that is orthogonal to the longitudinal and lateral dimensions. The splitter grating 104 in this embodiment has a pattern of optically dense regions, each having a longest dimension along the longitudinal dimension and being spaced substantially parallel to each other in the lateral dimension such that there are optically rare regions between adjacent optically dense regions. Each optically dense region has a depth in the transverse dimension that is smaller than a length in the longitudinal dimension. The splitter grating 104 is arranged with the longitudinal dimension at a shallow angle α relative to incident X-rays such that it is less than 30 degrees. In some embodiments, the splitter grating 104 can be similar in construction as the analyzer grating 114 and arranged similarly at a shallow angle α as described above with respect to the analyzer grating 114, although placed at a different position along the optical axis.

Figure 2B:
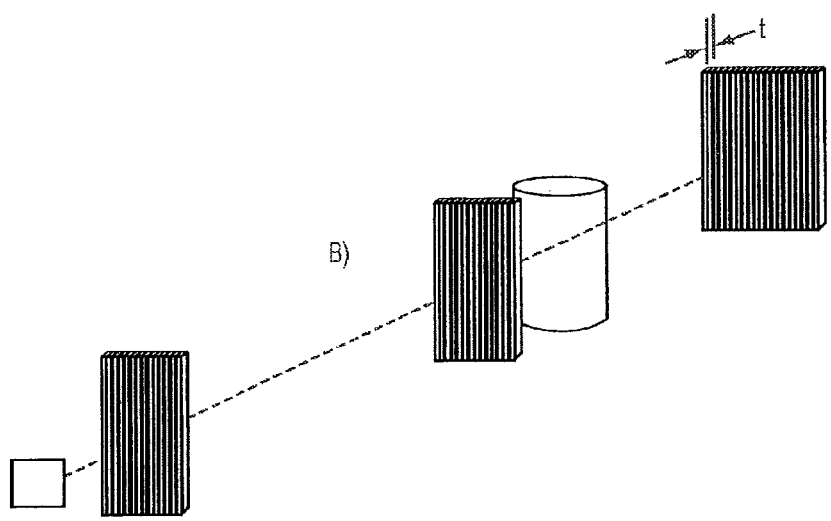
FIG. 2B is a schematic illustration of a conventional, normal incidence Talbot-Lau interferometer.

FIG. 2B is a schematic illustration of a conventional differential phase contrast X-ray imaging system that can be contrasted with the differential phase contrast X-ray imaging system 100 according to an embodiment of the current invention. In such a conventional system that is based on a Talbot-Lau interferometer, the gratings are arranged orthogonal to, and in some cases at slightly off-orthogonal angles to, the optical axis along which a beam of X-rays travels. As is illustrated in FIG. 2B, the longitudinal direction of the source, beam-splitter and analyzer gratings are all in the vertical direction of the illustration. The thickness of the grating t is the maximum depth of corresponding optically dense regions, such as parallel lines of gold or other high-Z material separated by regions of low-Z material, such as a silicon substrate. According to the conventional approach, one would have to increase the depth of the optically dense regions to operate with higher energy X-rays in order to sufficiently block the higher energy X-rays with the optically dense regions.

The current inventors recognized, and through experimentation demonstrated, that such gratings could be oriented as is illustrated in FIG. 2A such that incident X-rays would have to travel through much longer paths in the optically dense layers than the thickness t of the grating. Depending on the particular gratings, the paths the X-rays follow through optically dense material in the gratings can be orders of magnitude greater than the thickness t. However, since the gratings cause diffraction and interference effects due to the wave nature of the X-rays, it was difficult to predict either theoretically and/or numerically how such a change in geometry of the diffraction gratings would affect the X-ray beam. The current inventors thus developed and demonstrated the differential phase contrast X-ray imaging system 100, as illustrated schematically in FIG. 2A, by experimentation.

As used herein, the term "block" X-rays is intended to mean that sufficient attenuation is achieved relative to X-rays that pass through the optically rare regions of the grating to permit a useful contrast for the particular application. It is not intended to require absolutely 100% attenuation.

The splitter grating 104 and the analyzer grating 114 are arranged with a separation determined according to Talbot-Lau conditions according to some embodiments of the current invention. In some embodiments, the splitter grating 104 and the analyzer grating 114 have grating patterns that are determined according to Talbot-Lau conditions.

The X-ray illumination system 102, according to some embodiments of the current invention can include an X-ray source 116, and a source grating 118 arranged in an optical path between the X-ray source 116 and the beam splitter 104. The source grating 118 provides a plurality of substantially coherent X-ray beams when X-ray source 116 is a spatially extended source of X-rays, as is illustrated schematically in FIG. 2A. However, the broad concepts of the current invention are not limited to the particular embodiment illustrated in FIG. 2A. The X-ray illumination system 102 can include combinations of one or more gratings and mirrors, including both transmission and/or reflection gratings.

Figure 3A:
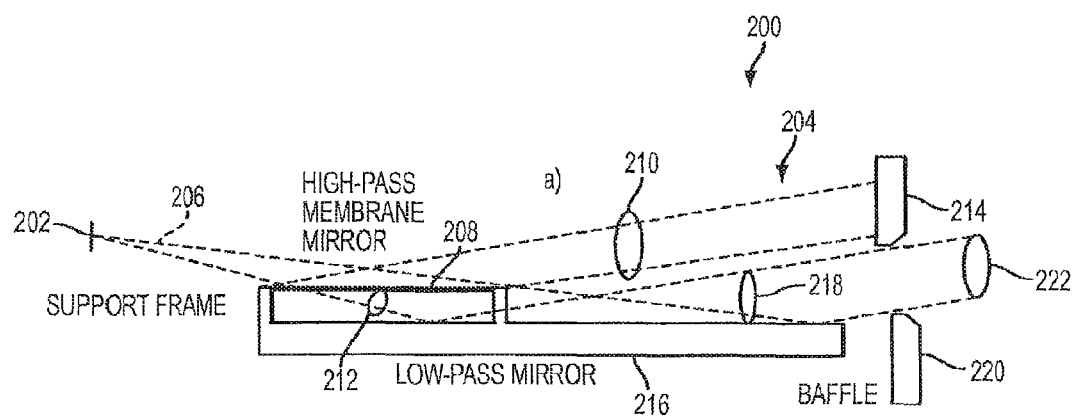
FIG. 3A is a schematic illustration of an X-ray illumination system that has a dual-mirror band-pass filter according to an embodiment of the current invention.

FIG. 3A is a schematic illustration of an X-ray illumination system 200 according to an embodiment of the current invention. The X-ray illumination system 200 can be used as part of the differential phase contrast X-ray imaging system 100 and/or any of the variations described above and/or can be used in conventional systems such as that illustrated in FIG. 2B, for example. For example, the X-ray illumination system 200 can be used for, or as a portion of, the X-ray illumination system 102. However, the X-ray illumination system 200 is not limited to only these particular applications.

The X-ray illumination system 200 has a poly-energetic X-ray source 202 and a band-pass filter 204 arranged in an optical path of X-rays 206 from the poly-energetic X-ray source 202. The band-pass filter 204 allows X-rays within a band of energies to pass more strongly than X-rays outside the band of energies. In an embodiment of the X-ray illumination system 200, the band-pass filter 204 includes a high-pass X-ray mirror 208 that reflects a first portion 210 of an incident beam of X-rays 206 that have energies less than a lower pass-band energy and allows a second portion 212 of the incident beam of X-rays to pass therethrough. The band-pass filter 204 also includes first beam stop 214 arranged to intercept and at least attenuate the first portion 210 of the incident beam of X-rays 206 that have energies less than the lower pass-band energy, a low-pass X-ray mirror 216 that reflects a portion 218 of the second portion 212 of the incident beam of X-rays 206 after passing through the high-pass X-ray mirror 208 that have energies less than a upper pass-band energy, and a second beam stop 220 arranged to intercept and at least attenuate X-rays that miss the high-pass X-ray mirror 208 prior to reaching the second beam stop 220. The first and second beam stops (214, 220) are arranged to allow a beam of X-rays 222 having energies between the upper pass-band energy and the lower pass-band energy to pass therethrough. The band-pass filter 204 is not limited to the particular example illustrated in FIG. 3A. In other embodiments, more than three mirrors can be used, for example. The X-ray illumination system 200 provides a more monochromatic beam of X-rays than that of the X-ray source 202. Furthermore, reflection and/or transmission gratings can be used in combination with the band-pass filter 204 to improve coherence of the X-rays from the poly-energetic X-ray source 202. In further embodiments, a combination of high-pass mirrors and at least one low-pass mirror can provide combined improved coherence and chromaticity of X-rays from the poly-energetic X-ray source 202.

The low-pass X-ray mirror can be a membrane X-ray mirror, for example, that has a reflecting layer that is a high-Z material on a support layer that is a low-Z material. Z is the atomic number. The term "high-Z material" is intended to mean materials that include atomic elements with Z at least 42 (for example, but not limited to Rh, Pt, and/or Au) so as to have a relatively strong reflectivity for the X-rays. The term "low-Z material" is intended to mean materials that include atomic elements with Z less than 14 (for example, but not limited to C, Si, quartz, and/or glass) so as to have a relatively low reflectivity for the X-rays.

The following are some new elements according to some embodiments of the current invention, as contrasted to conventional system:
  i) The use of micro-periodic gratings having the absorbing bars tilted at a glancing angle along the direction of the incident radiation as in FIG. 2A
  The tilting of the gratings is a modification of the conventional Talbot-Lau interferometer at normal incidence (FIG. 1B). Although this modification appears simple, it is difficult to foresee theoretically that a glancing incidence Talbot-Lau interferometer will work with extended sources. We arrived at this idea following the concept of 'physical period' mirrors and could verify that it works only through direct experimentation.
  ii) The use of micro-periodic gratings at glancing angle in conjunction with simple or micro-periodic X-ray mirrors.
  As further discussed, one embodiment of the current invention uses a simple total reflection X-ray mirror at grazing incidence to select the spectral region where the interferometer has highest contrast. In another embodiment the source grating is replaced by a micro-periodic mirror in the 'physical period' geometry described in Ref. 7, which combines in a single optical element the spectral filtering and the production of quasi-coherent radiation.
  iii) The use of spectral band-pass multilayer X-ray mirrors in conjunction with tilted gratings.
  In another embodiment of the invention, graded multilayer mirrors are used as a spectral filter or as a 'source grating', for further improved interferometer contrast and angular sensitivity.
  iv) The use of energy-resolving detectors to select the spectral region of maximal interferometer contrast.

The phase-contrast imaging system of the example illustrated in FIG. 2A includes three micro-periodic gratings in a Talbot-Lau interferometer configuration, tilted at equal glancing angles $\alpha$, in the range from a few degrees to a few tens of degrees. The period of the gratings can be a few μm (e.g., but not limited to, $g0=g1=g2=5$ μm) and the grating inter-distances and periods follow the equations of the normal incidence Talbot-Lau interferometer. The first grating is a 'source grating', which produces an array of quasi-coherent line sources from an extended incoherent source. The second grating is a beam-splitter which produces a high contrast fringe pattern (the 'Talbot pattern') at the analyzer location when illuminated through the source grating. Lastly, an analyzer grating is used to transform changes in the Talbot pattern into intensity changes on a 2-D X-ray detector.

The system works similarly to the conventional, normal incidence Talbot-Lau interferometer [2,3], sketched for reference in FIG. 2B. When a refractive object is placed in the X-ray beam ("Object" in FIG. 2A) it perturbs the Talbot pattern produced by the beam-splitter. The analyzer transforms this perturbation into an intensity change on the detector, which enables imaging and quantifying the X-ray refraction and scatter induced by the object.

The source and analyzer gratings can be conventional, commercially available absorption gratings made, for example, by filling the gaps in a silicon or photoresist grating with gold, as described in Refs. [5, 6]. The beam-splitter can be a π-shift phase grating, also can also be made in the conventional manner.

However, according to some embodiments of the current invention, the gratings are tilted at a glancing angle and have the absorbing bars along the direction of the incident radiation, as shown schematically in FIG. 2A. Our experiments demonstrated that this modification of the Talbot-Lau setup solves in a simple and practical manner the problem of DPC imaging at high energy.

Indeed, an obstacle to the use of normal incidence Talbot-Lau interferometers at high energy is the practical limit in the thickness of small period source and analyzer gratings [5,6]. To obtain high interferometer contrast or visibility the absorbing bars of the source and the analyzer gratings must be strongly attenuating (typically around 90-95%). At the same time, the X-ray absorption of any material decreases rapidly as the X-ray energy is increased. This is illustrated in FIG. 4 which shows, as a function of energy, the Au thickness needed to absorb 95% of the incident X-rays. As one can see, the thickness needed for efficient absorption at E>40 keV is > several hundred μm.

At present, however, it is not technologically possible to make absorption gratings with a few micron periods and several hundred μm thickness. The current limit in the grating aspect ratio (ratio between bar thickness and width) is around 50, while, as shown above, aspect-ratios of several hundred would be needed to make high contrast interferometers for high energy. This fact is confirmed by experiment. Thus, attempts to build a Talbot-Lau interferometer of 60 keV mean energy using normal incidence gratings had little success: the fringe contrast was of only several %. The same effect can be seen in FIGS. 5A and 5B below. Note however that phase gratings for high energy can easily be made, since they need to be much thinner [2,3,7,8].

Some embodiments of the current invention can provide a simple, practical and also economical solution to this problem: by tilting the gratings at a glancing angle $\alpha$, the effective absorber thickness in the X-ray path increases to $t/\sin(\alpha)$, with t the physical or normal incidence thickness of the grating. For instance at $\alpha \sim 10°$ the effective thickness increases by a factor of 6. Thus, a 100 µm thick, 5 µm period grating, which is within the present technological capability, appears as a grating of 600 µm thickness when tilted at a glancing angle of 10° in the direction of the radiation.

The physical thickness of the beam-splitter is simply that required to produce a $\pi$-phase shift at the desired design energy $E_0$, when viewed by X-rays incident at an angle $\alpha$; for instance, if t(0) is the thickness needed for normal incidence operation at $E_0$, the thickness required at glancing incidence $\alpha$, is $t*\sin(\alpha)$.

Figures 5A, 5B:
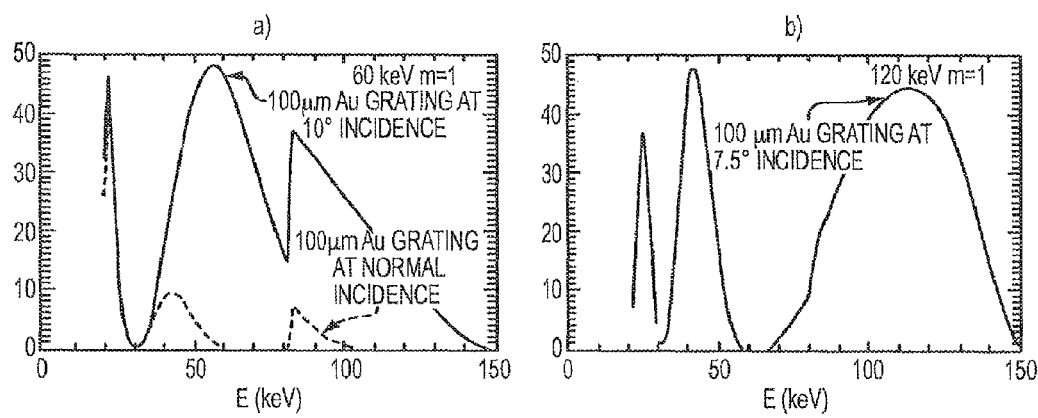
FIG. 5A shows computed contrast for 5 μm period, m=1 interferometer of 60 keV mean energy, using 100 μm thick Au source and analyzer gratings at normal incidence and at 10° incidence to contrast an embodiment of the current invention with a conventional system.
FIG. 5B is similar calculation as in FIG. 5A, but for interferometer of 120 keV design energy, using 100 μm thick Au source and analyzer gratings at 7° incidence. The grayed part of the curve represents low energy peaks that are removed by absorption of the low energy photons in the object or using a separate spectral filter.

Some embodiments of the current invention can enable, in this way, building high contrast Talbot-Lau interferometers up to very high X-ray energy. This is shown in FIG. 5A which plots the computed contrast as a function of energy for an interferometer having 100 µm thick gratings at normal incidence, and at 10° glancing incidence angle. The beam-splitter is a Ni phase grating having t(0)=20 µm for a mean or 'design' energy of 60 keV. The duty-cycle (gap width/period) of the source grating is 37% and the Talbot order is m=1.

As shown in FIG. 5A, tilting the gratings produces a dramatic contrast increase for energies above 40 keV approximately. In particular, good contrast obtains in the 40-70 keV range, which is of high interest for medical phase-contrast imaging because in this range the soft tissue dose is at a minimum [1]. In addition, appreciable contrast obtains also above the Au K-edge at 80 keV.

As one can see for example with reference to FIG. 5A, some embodiments of the current invention can provide high contrast interferometers for even higher X-ray energies. This is illustrated in FIG. 5B which plots the computed contrast for an m=1 interferometer having 100 µm thick Au source and analyzer gratings, tilted at 7°. The phase grating in this case is made of gold and has t(0)=10 µm, for a 120 keV design energy. The source grating duty-cycle is 37%. As seen, a broad band of high interferometer contrast obtains in the region ~90-130 keV. The capability for operation at these high energies makes some embodiments of the current invention also of strong interest for NDT and security applications.

Figure 6:
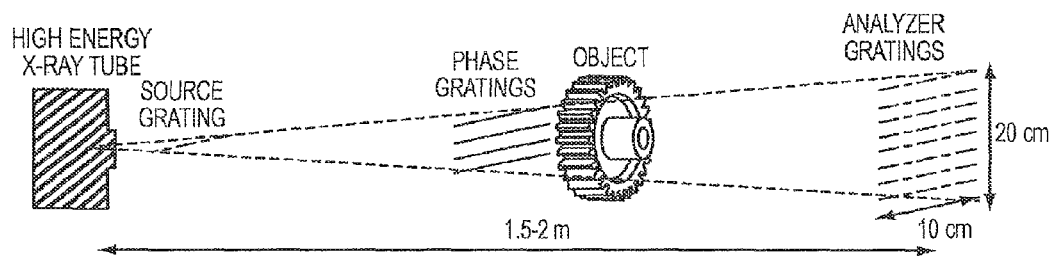
FIG. 6 is a schematic illustration of a differential phase contrast X-ray imaging system according to an embodiment of the current invention that has a large field of view.

At the same time, some embodiments of the current invention can allow one to obtain interferometers with sufficiently large fields of views for medical and other practical applications. For instance, a commercially available 70×70 mm analyzer grating would enable one to obtain a ~12×70 mm field of view at 10° incidence and a 9×70 mm field of view at 7° incidence. In addition, it is easy to make high energy imaging systems with larger fields of view by stacking multiple tilted gratings, as is illustrated schematically in FIG. 6.

As mentioned, although the modification of the Talbot-Lau interferometer according to some embodiments of the current invention appears at a first look straightforward, it is nevertheless difficult to predict theoretically or computationally that a glancing incidence setup with the grating bars oriented along the direction of the incident X-rays as in FIG. 2A, can work with a spatially extended X-ray source. While glancing angle grating Talbot interferometers have been discussed in the literature [10,11], the grating bars have been always oriented perpendicularly to the direction of the incoming radiation (i.e., the 'effective period' geometry discussed in Ref. 7). In this geometry, however, the grating contrast at high energy does not improve when tilting the gratings, because the effective X-ray path through the absorber decreases instead of increasing.

We thus developed embodiments of the current invention experimentally using a Talbot-Lau interferometer having gratings tilted at a glancing angle of 22.5° and operated at ~43 keV mean energy. All the gratings had equal period of 10 µm, with the source grating having 55 µm thick Au bars and the analyzer 100 µm thick Au bars. The phase grating was a 23 µm thick Si grating tilted at the same angle of 22.5°. All the gratings had 50% duty cycle. The interferometer was operated in the first Talbot order using as X-ray source an extended spot W anode tube at 60 kVp. To obtain a spectrum with around 43 keV mean energy the tube output was filtered with a 100 mm thick water layer and with a 65 µm Cu. The computed spectrum incident on the gratings is shown in the right panel of FIG. 7C.

Figures 7A, 7B, 7C:
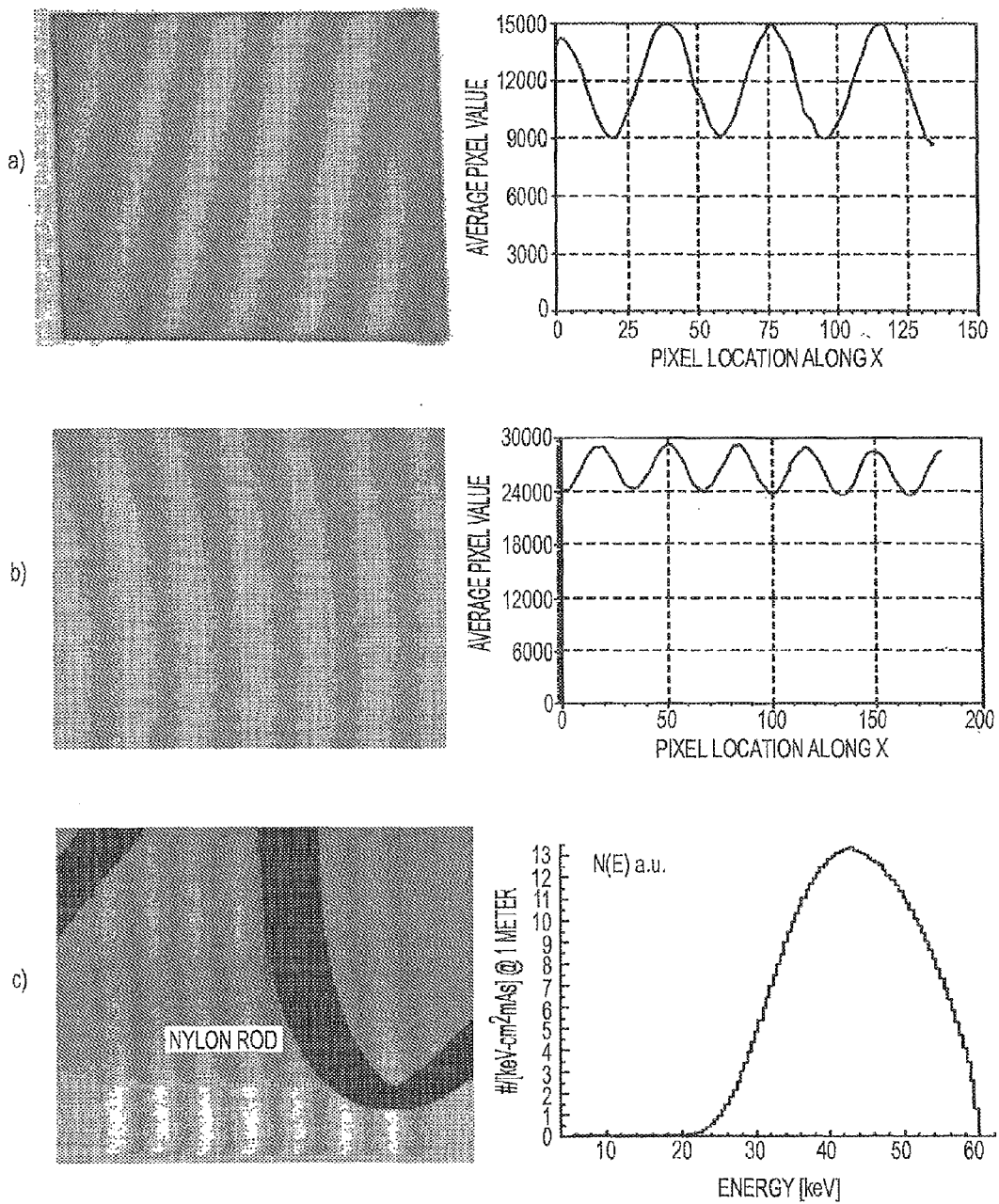
FIG. 7A shows a Moiré pattern and intensity profile obtained with glancing angle (22.5°) Talbot-Lau interferometer and with spectrum of ~43 keV mean energy according to an embodiment of the current invention.
FIG. 7B shows similar data, but for normal incidence interferometer.
FIG. 7C shows Moiré fringe shifts produced by a 12 mm nylon rod with tilted grating interferometer according to an embodiment of the current invention. The right panel shows the X-ray spectrum for FIGS. 7A and 7B.

A Moiré fringe pattern produced by the tilted gratings is shown in the left panel of FIG. 7A, while a lineout through the pattern is shown in the right panel. The fringe contrast is defined as: $V=(I_{max}-I_{min})/(I_{max}+I_{min})$. As one can see, using tilted gratings can provide good interferometer contrast (V~25%) at high X-ray energy. Even higher contrast would be obtained with a 100 µm thick source grating, similar to the analyzer one.

For comparison, FIG. 7B illustrates the limited contrast that can be obtained with Talbot-Lau interferometers using normal incidence gratings. The Moiré pattern in this case has been obtained using 5.4 µm period gratings, with source and analyzer gratings having nominally 100 µm thickness, which is about the technological limit for this period. The phase grating was a 15 µm thick Ni grating designed for 40 keV mean energy. The incident spectrum was the same as in FIG. 7A. As can be seen, the best achievable normal incidence contrast is more than twice lower (V~11%) than at glancing incidence. In addition, the contrast of the glancing incidence interferometer can easily be pushed to even higher values by further tilting the gratings.

Lastly, FIG. 7C demonstrates that the glancing angle Talbot-Lau interferometer performs phase-contrast measurements similar to the normal incidence one. The left panel in FIG. 7C shows the perturbed Moiré pattern obtained with the tilted gratings when imaging a nylon rod of 12 mm diameter. (The opaque object in the image is a Sn wire of 1.5 mm diameter). As can be seen in FIG. 7C, while the nylon rod is almost transparent to X-rays, it nevertheless produces strong Moiré fringe shifts near its edges.

In conclusion, our experimental results indicate that imaging systems based on glancing incidence Talbot-Lau interferometers offer a simple but powerful solution to differential phase-contrast imaging at high X-ray energy. In addition, since the above results were obtained with a thick water layer in the X-ray path, they directly demonstrate that the systems in the Invention can work for phase-contrast imaging of thick body parts using conventional X-ray tubes. So far, this possibility was demonstrated only using synchrotron X-ray sources.

The tilted grating Talbot-Lau interferometer concept described herein can be directly applied for X-ray phase-contrast imaging at high energy without any further development. This is particularly the case for applications in which the angular sensitivity of m=1 Talbot-Lau interferometers is sufficient (the angular sensitivity increases with the Talbot order m as √m, with m=1, 3, 5 . . . ). Example of such situations would be ultra-small angle scattering (USAXS) imaging systems for non-destructive testing and studies of micro/nano structured matter in material sciences, nanotechnology, or industry. High energy m=1 tilted grating systems could also be of interest for medical bone phase-contrast imaging, since bone is a strong USAXS scatterer.

For refraction based soft tissue imaging at high energy the angular sensitivity of m=1 interferometers is likely too low because the refraction angles scale as $1/E^2$. To make high energy Talbot-Lau interferometers that also have high angular sensitivity, one must work in higher (m>3) Talbot orders. At high-m however the spectral region of good contrast gets narrower (width ~1/m) and spectral filtering can be employed to maintain good interferometer contrast [8]. Thus combining the glancing angle grating concept with the X-ray mirror filtering concept can be useful for some applications.

Another alternative embodiment would be to use energy resolving detectors to select the spectral region of high interferometer contrast. In FIG. 5B, this would be for instance the region between 90 keV and 130 keV approximately. 2-D pixilated detectors such as CdTe arrays exist nowadays that have high energy resolution, high quantum efficiency and good photon counting capability, at energies up to a few hundred keV. This novel approach is of particular interest for situations that can tolerate a higher radiation dose, such as in industrial applications, since a large flux of photons outside the region of high interferometer contrast would not be detrimental.

Figure 8A:
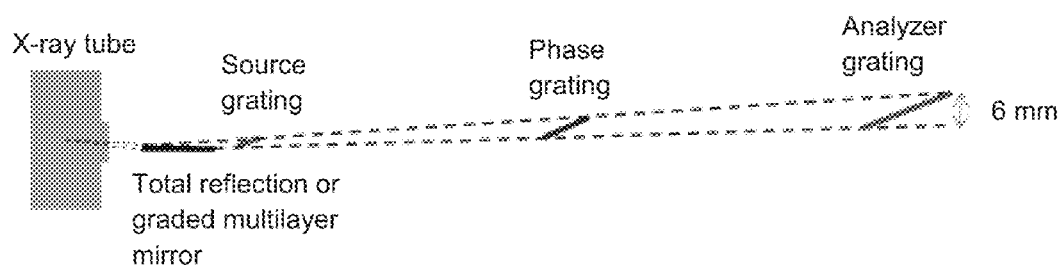
FIG. 8A is a schematic illustration of a differential phase contrast X-ray imaging system according to an embodiment of the current invention that has glancing angle gratings for phase-contrast imaging and a laterally graded multilayer mirror for quasi-monochromatic spectral filtering.
Figure 8B:
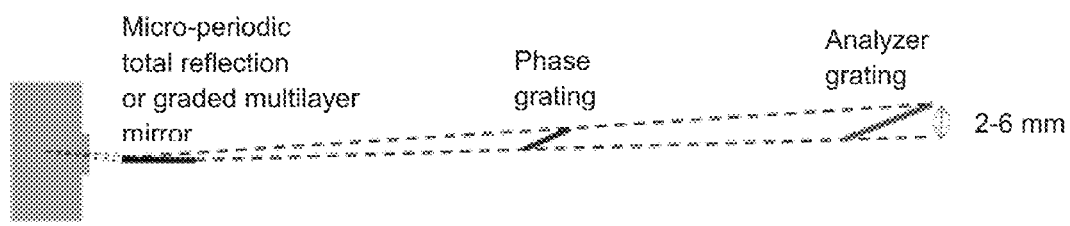
FIG. 8B is a schematic illustration of a differential phase contrast X-ray imaging system according to an embodiment of the current invention that is similar to the embodiment of FIG. 8A, but uses a micro-periodic mirror instead of the source grating.

Other alternative embodiments can include the following two basic variations:
1) High energy phase-contrast imaging systems using only glancing angle gratings, such as in FIG. 2A.
One embodiment for this variation is a high energy m=1 DPC imaging system using an energy resolving detector to discriminate the photons outside the region of high contrast. An example application for such a system would be phase-contrast based non-destructive testing of composite metallic parts in the aerospace and aviation industry.
2) High energy phase-contrast imaging systems combining glancing incidence gratings with total reflection or Bragg reflection (multilayer) mirrors, such as in FIGS. 8A and 8B.
The mirror can be a simple, non-patterned mirror that serves only as spectral filter (FIG. 8A), or it can be a micro-periodically patterned mirror having strips parallel to the incident X-rays (the 'physical period' geometry described in Ref. 7) that would replace the source grating (FIG. 8B). In the latter case the mirror would serve simultaneously as spectral filter and spatial filter, thus reducing the number of optical elements and simplifying the setup. Further, the mirror can be either a total reflection mirror working at angles around 1-1.5 mrad, or a graded multilayer mirror working at larger angles of several mrad.

An embodiment of such a system would be an m=5 interferometer for the tungsten K-shell line emission between ~60-70 keV. This quasi-monochromatic emission can be made very bright using W anode tubes at high voltage (few hundred kV). In addition, as mentioned, this energy region is ideal for medical phase-contrast imaging deep in the human body.

Figure 9:
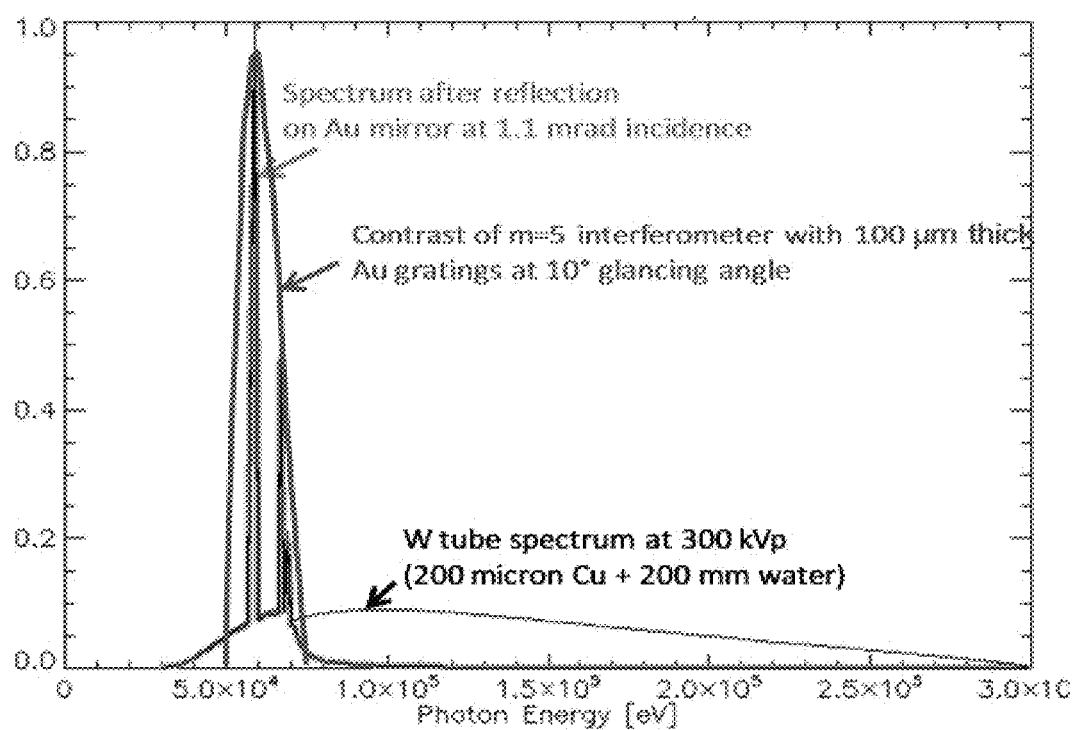
FIG. 9 shows a computed spectrum of 300 kVp W anode tube after transmission through 200 mm of soft tissue and 200 μm Cu. Also shown the spectrum after reflection on a Au mirror at 1.1 mrad, together with the contrast of an m=5 interferometer having 100 μm thick Au gratings at 10° incidence angle.

The principle of this embodiment is sketched in FIG. 9. The total reflection on the mirror effectively cuts off the high energy portion of the spectrum, which would contribute to the dose without contributing to the phase contrast image [8]. The low energy part of the spectrum is cut off by an absorption filter. The mirror/filter combination produces thus a quasi-monochromatic band of radiation that matches well the contrast curve of an m=5 Talbot-Lau interferometer (FIG. 9).

The filtering mirror can also be a laterally graded synthetic multilayer mirror, which can reflect only a narrow band between ~60-70 keV, allowing thus to work in even higher Talbot orders (e.g. m=9) and thus to achieve even higher angular sensitivity and interferometer contrast. Lastly, the mirror can be micro-periodically patterned and thus fulfill simultaneously the function of spectral filter and of source grating.

The field of view of systems combining glancing angle gratings with grazing incidence mirrors such as in FIG. 8 is smaller in the vertical dimension than for pure tilted grating systems. A typical value is of several mm by several cm. Nevertheless, one can stack multiple such mirror/glancing incidence grating interferometers in order to obtain a larger field of view, similar to FIG. 6. This possibility has been in fact demonstrated experimentally for conventional X-ray imaging in Ref. 10, where tens of laterally graded multilayer mirrors have been stacked one upon the other to make a large area (~10×20 cm) quasi-monochromatic radiographic system.

DETAILED DESCRIPTION REFERENCES

1. S.-A. Zhou and A. Brahme, *Physica Medica* 24 129 (2008)
2. Momose A, Yashiro W, Takeda Y, Suzuki Y and Hattori T, *Japanese Journal of Applied Physics* 45 5254 (2006)
3. Pfeiffer F, Weitkamp T, Bunk O and David C, *Nature Physics* 2, 258 (2006)
4. Tilman Donath, Franz Pfeiffer, Oliver Bunk, et al., Rev. Sci. Instrum. 80, 053701 (2009)
5. David C, Bruder J, Rohbeck T, Grunzweig C, Kottler C, Diaz A, Bunk O and Pfeiffer F, *Microelectronic Engineering* 84, 1172(2007)
6. Reznikova E, Mohr J, Boerner M, Nazmov V, Jakobs P-J, *Microsyst. Technol.* 14 1683(2008)
7. D. Stutman, M. Finkenthal, N. Moldovan, *Applied Optics* 49, 4677(2010)
8. D. Stutman, T. Beck, J. Carrino and C. Bingham, *Phys. Med. Biol.* 56, (5697) 2011
9. Y. Park, S. Han, J. Chae, C. Kim, K. S. Chon, H.-K. Lee and D. S. Han, *Proc. SPIE* 7258 Medical Imaging 2009: Physics of Medical Imaging, 72583L (2009)
10. M. Testorf, J. Jahns, N. A. Khilo, and A. M. Goncharenko, Opt. Commun. 129, 167-172 (1996)
11. Han Wen, Camille K Kemble, and Eric E. Bennett OPTICS EXPRESS 19, 25093(2011)

Further Embodiments and Examples

The following examples analyze the angular sensitivity needed for refraction enhanced imaging with the Talbot method and proposes ways to optimize the Talbot setup for improved refraction based imaging with conventional X-ray sources. Even though we use examples from medical and high energy density (HED) plasma imaging, the conclusions apply also to other fields, such as material sciences, NDT, or security.

Figure 10:
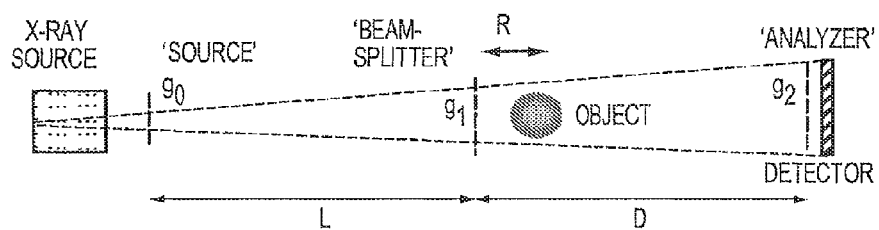
FIG. 10 is a schematic illustration of a Talbot-Lau grating interferometer with conventional X-ray source.

The Talbot interferometer is based on the Talbot effect, which consists of the production of micro-fringe patterns by a 'beam-splitter' grating illuminated by X-rays, at the so called Talbot distances $d_T = m\, g_1^2/8\lambda$, where $\lambda$, is the wavelength, $g_1$ is the grating period, and $m=1, 3, 5\ldots$ is the order of the pattern. The basic interferometer consists of the beam-splitter (typically a π-shift phase grating) followed by an 'analyzer' absorption grating of period $g_2$ equal to that of the Talbot fringe pattern and placed at the magnified Talbot distance $D \sim d_T/(1-d_T/L)$ from the beam-splitter, where L is the distance between the source and the beam-splitter (FIG. 10). When a refractive object is introduced in the X-ray beam the Talbot pattern is shifted, leading to intensity changes behind the analyzer approximately proportional to the angle of refraction of the X-rays. Since hard X-rays are deflected by only a few μ-radians in low-Z matter, $g_2$ must be of the order of a few μm and D of the order of the meter to achieve sufficient angular sensitivity. In addition, to make the interferometer work with extended, incoherent X-ray sources, a third, absorption grating having period $g_0 = g_2 \cdot L/D$ and openings of width $s_0 \leq g_0/2$ is placed near the source, effectively dividing it into an array of quasi-coherent micro-sources. This choice of period and opening width ensures that the Talbot patterns from each micro-source constructively add at the analyzer, for any L and D combination [13-15, 19-21].

The interferometer is characterized by the angular width or resolution $W \sim g_2/D$, which determines its angular sensitivity $S = 1/W$, and by the mean energy $\langle E \rangle$, and spectral width $\Delta E$, of the region of high fringe contrast, which determine its spectral response. Typical angular widths are in the 5-10 μ-radian range and typical contrast values are ≤ few tens of percent when working with conventional X-ray sources [20,21]. In addition, as discussed in Ref. 19, the effective angular sensitivity of the Talbot interferometer $S_{eff}$, decreases proportional to the distance R between the beam-splitter and the object; for instance, $S_{eff} = S \cdot (1-R/D)$ if the object is placed behind the phase-grating as in FIG. 10. The decrease comes from the fact that the refraction angle 'seen' by the beam-splitter at a distance R is smaller than that at the object [19].

One can thus define an effective angular width for the Talbot interferometer as $W_{eff} = 1/S_{eff}$ and summarize the two conditions that must be simultaneously met to achieve substantial refraction contrast enhancement with the Talbot method: (i) high interferometer contrast and (ii) effective angular width comparable to the range of refraction angles produced by the object.

Mean energies possible with grating interferometers are up to a few tens of keV, with spectral widths $\Delta E/\langle E \rangle \sim 1/m$, where m is the Talbot order [13-15, 20-21]. The upper energy bound is due to technological limits in the fabrication of thick, micron-period absorption gratings [22, 23]. The optical transmission or throughput of the Talbot interferometer for divergent and polychromatic light is much higher (up to 10-20%) than for crystal ABI systems. The Talbot method can thus efficiently utilize the spectrally broad and divergent emission produced by conventional X-ray sources. The field of view is limited by the practical grating size at <10×10 cm approximately.

While the Talbot method is attractive for practical applications, as above mentioned the results so far indicate that its refraction contrast is lower than that of the crystal method. It is thus useful to briefly compare the two methods in order to delineate the fundamental differences. This can be done by comparing the 'phase-scan' intensity curve in the Talbot method [14,15] with the rocking curve of the analyzer crystal in the ABI method [5]; these curves play an equivalent role in refraction based imaging as discussed in the following.

The phase-scan technique is illustrated with a numerical simulation in FIGS. 11A-11D. To compute refraction images we use throughout these examples the XWFP code in conjunction with the XOP database [24, 25]. XWFP computes the X-ray wave propagation, including absorption, refraction and diffraction, through objects such as rods, spheres, and cavities, and through optical elements such as phase and absorption gratings. The XOP database allows computing δ and β for materials of arbitrary composition, by specifying the mass fraction for each element and the mass density of the compound.

We simulated spectrally averaged refraction images for an interferometer having a 'symmetric' design in which L=D and gratings of equal period of 10 μm. The absorption gratings had 60 μm thick gold bars and the phase grating 25 μm thick Si bars, for a mean energy of 20 keV. The interferometer was set in the third Talbot order (L=D=1.2 m), with R=1 cm ($W_{eff} \sim W = 8.3$ μ-radian)). We assumed the source is a 60 μm spot W anode X-ray tube operated at 25 kV($\langle E \rangle \sim 20$ keV), exposure of 10 mA·s, and a detector having 20% quantum efficiency and 50 μm resolution. As test object we used a 1 mm diameter Be rod in water medium, producing refraction angles in the range $\leq \alpha_M = \pm 4$ μ-radian. A 100 μm diameter X-ray opaque Au wire was also included in the simulation to provide a contrast reference. The spectrally averaged images were obtained by weighting monochromatic images computed at 0.5 keV intervals with the W tube power spectrum and by including statistical photon noise.

Figures 11A, 11B, 11C, 11D:
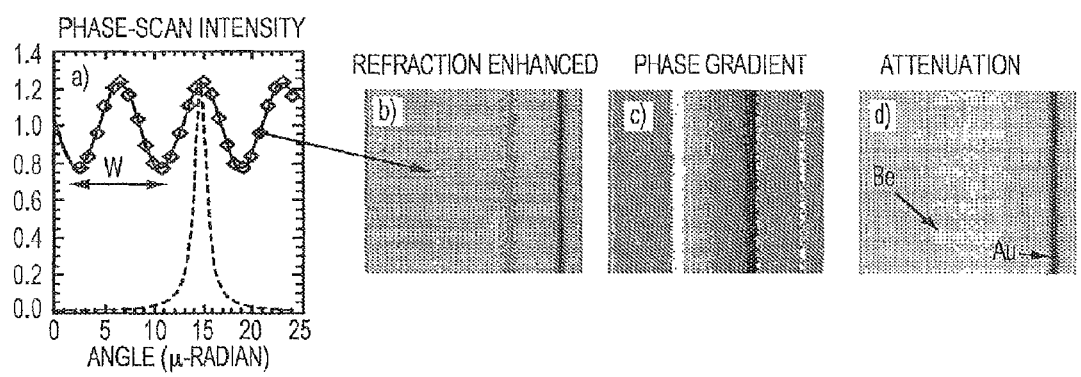
FIG. 11A-11D show simulated phase-scan curve (a), refraction enhanced image (b), phase-gradient image (c), and attenuation image (d), of 1 mm Be rod in water medium. We assumed an m=3, <E>=20 kV, 10 μm period symmetric interferometer of 2.4 m length and a W anode tube as source. A 100 μm diameter Au wire was also included as a contrast reference. A typical rocking crystal curve in the ABI method is also plotted in FIG. 11A.

The phase-scan curve obtained by scanning the analyzer position in 30 steps of size z=1 μm is shown in FIG. 11A. For comparison with the crystal method we plotted the ordinate in units of angle spanned by the phase-scan, $\theta \sim k \cdot z/D$, $k=0, 1, \ldots$, with z the step size. The maxima of the phase-scan modulations represent the 'bright-field' (BF) intensity and the minima the 'dark-field' (DF) intensity [15]. The normalized difference between these intensities can be used to define the interferometer contrast, $V_{Talbot} = (I_{BF} - I_{DF})/(I_{BF} + I_{DF})$. This definition is similar to that of the Talbot fringe contrast or visibility [20,21], while characterizing the overall interferometer contrast. The computed contrast values in FIG. 11A match well those obtained experimentally with Talbot interferometers operated with conventional X-ray tubes [13-17].

FIG. 11B shows the raw, refraction enhanced image obtained at an interferometer position in the middle of the quasi-linear portion of the phase-scan curve, as indicated by the arrow. Refraction contrast of ~20% obtains at edges of the Be rod, showing that the Talbot method can produce contrast enhancements of the order of $\alpha_M/W_{eff}$, even without phase-scanning.

FIGS. 11C and 11D show the output of the phase retrieval procedure. FIG. 11C shows the phase gradient or 'pure refraction' image, in which the intensity is proportional to the refraction angle, while FIG. 11D shows the 'pure attenuation' image [14,15]. The analysis was done using the Fourier method described in Ref. 15. FIGS. 11B to 11D illustrate the potential of refraction based imaging: while the weakly absorbing Be object is almost invisible in the attenuation image, it appears with good contrast in the phase gradient and in the refraction enhanced images.

To make a quantitative comparison between the Talbot method and the crystal one we also plotted in FIG. 11A a Lorentzian of 1.5 μ-radian FWHM, approximating the typical rocking curve of the analyzer crystal in the ABI method [5]. By comparing the angular width $W \sim g_2/D$ of the Talbot phase-scan modulation with the angular width of the crystal rocking curve one can thus directly compare the angular sensitivity of the two methods. An approximate comparison between the contrast of the two methods can also be made by defining an equivalent 'crystal contrast' $V_{crystal}$ as above and by using as $I_{BF}$ the intensity at the peak of the rocking curve and as $I_{DF}$ the intensity in its wings, for instance at one FWHM distance away from the peak.

Three basic differences between the two methods are apparent from this comparison:

First, the typical crystal angular width is several times smaller than that of the Talbot interferometer ($W \sim 8.5$ μ-radian in FIG. 11A).

Secondly, the equivalent crystal contrast is also substantially higher, $V_{crystal} \sim 67\%$, as compared to $V_{Talbot} \sim 25\%$.

Thirdly, FIG. 11A shows that the Talbot interferometer works as a periodic angular filter, while the crystal filters only a narrow angular range. Thus, the Talbot interferometer does not reject X-rays scattered at angles higher than its angular width, while the crystal does. The rejection of scattered radiation is deemed to be an important factor in the superior performance of the ABI method [1-5].

This discussion raises two questions: (i) how does the typical angular width of the Talbot method compare to the range of refraction angles expected in applications, and (ii) how can the angular sensitivity and contrast of the Talbot method be made closer to that of the crystal method. The first point is discussed in the following.

Range of X-Ray Refraction Angles in Practical Applications

To assess how the angular width of the Talbot method compares with the X-ray refraction angles encountered in typical applications we considered two practical examples: the refraction of hard X-rays in a HED plasma and the refraction in soft issues such as cartilage, tendon and muscle.

The Case of HED Plasma Radiography.

In the typical HED plasma radiography a micron sized X-ray backlighter (usually a laser produced plasma) illuminates a sub-mm, low-Z plasma target of many times the solid density, such as an imploding IFE (Inertial Fusion Energy) capsule. High spatial resolution requires imaging at high magnification (M~10-100) [11,26,27].

To estimate the refraction angles in IFE radiography we modeled the imploding capsule as concentric layers of Be and H having and 0.4 mm and 0.3 mm diameter respectively, and 0.1 mm thickness and 6 g/cm$^3$ density each. For the imaging setup we assumed a distance between the backlighter and the capsule of 7.5 cm and L=D=2 m (R=1.9 m). In this setup the beam-splitter could be sufficiently far from the imploding capsule to survive the implosion when placed behind a protective filter [26,27]. However, since the imaged object is far from the beam-splitter, the effective angular sensitivity is reduced as above discussed, by the factor $(1-R/L) \sim 0.05$.

Figure 12:
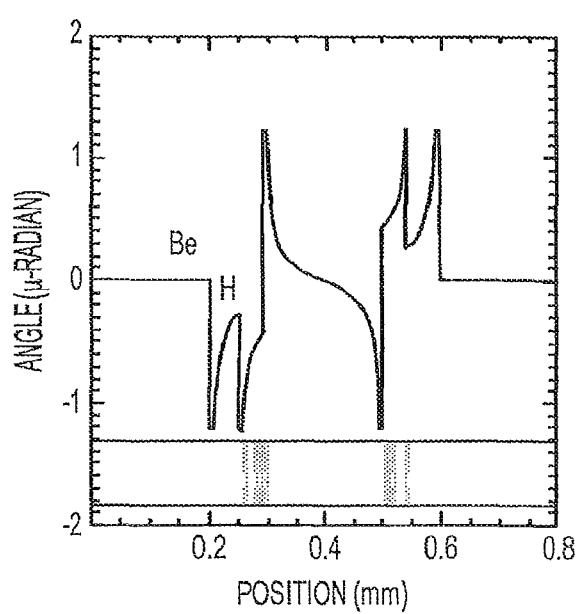
FIG. 12 shows computed refraction angles for IFE capsule model at 22 keV. The attenuation image is also shown as inset.

FIG. 12 shows the range of refraction angles incident on the beam-splitter for a typical backlighter energy of 22 keV (Ag K-α, [27]). As seen, while the refraction contrast enables one to discriminate the Be and H layers (otherwise invisible in the attenuation image), the range of refraction angles is small, $\alpha_M \leq \pm 1$ μ-radian.

The Case of Soft Tissue Radiography.

Soft tissue imaging is one of the most investigated applications of the Talbot method. The synchrotron experiments show for instance that X-ray refraction enables imaging of joint soft tissues such as cartilage or tendon, which are important in the diagnostic of arthritis [1,4,18]. To estimate the typical refraction angles for soft tissues we assumed the case of a small joint and used a simple numerical model or 'phantom' to compute its attenuation and refraction angle profiles. The phantom consisted of layers of materials simulating bone, cartilage, synovial fluid, connective tissue of the joint capsule, tendon, and skeletal muscle (inset in FIG. 13), approximating the anatomy of a human proximal finger joint. To compute δ and β for the joint soft tissues we used the composition and density of body tissues from the compilation by Woodard and White [28].

Figure 13:
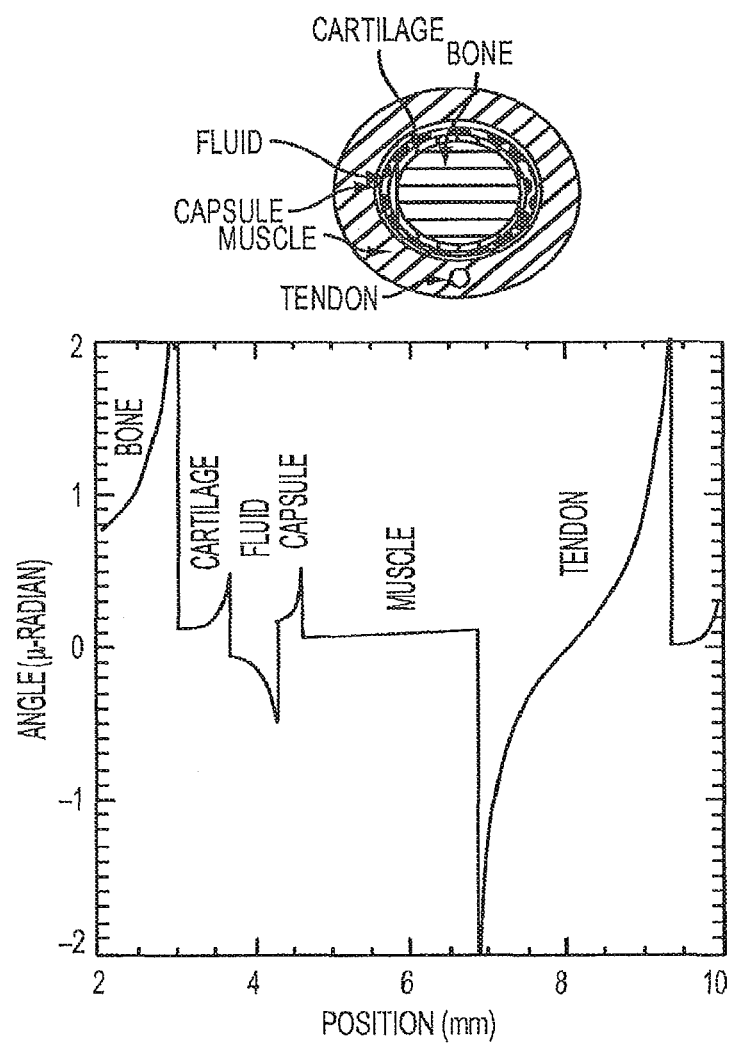
FIG. 13 shows computed refraction angles for small joint phantom at 25 keV. The layout of the joint phantom is shown at the top.

The refraction angles for the small joint phantom at 25 keV are shown in FIG. 13. As can be seen, with the exception of the bone/cartilage and of the tendon/muscle combinations, the range of refraction angles for cartilage, fluid and joint capsule is very small, $\alpha_M$ in the range of a few tenths of a μ-radian. This is due to the small difference in index of refraction between soft issues (e.g., several % for cartilage and joint fluid). These very small refraction angles predicted by our model are also in agreement with the synchrotron experiments; for instance, Shimao et al. estimated refraction angles in the range 0.1-0.4 μ-radian for a human finger joint at 36 keV [18].

The conclusion from the above is that the substantially larger width characteristic of Talbot interferometers, as well as their lower intrinsic contrast, can make soft tissue imaging with conventional X-ray sources challenging. A somewhat similar situation occurs in IFE DPC radiography for geometries where the beam-splitter is placed far from the target plasma. Ways must thus be explored to optimize the Talbot setup for maximal angular sensitivity and contrast, as further discussed.

Optimization of the Talbot Setup for High Angular Sensitivity and Contrast

With the notations in FIG. 10, in a magnifying geometry the angular width W of the Talbot interferometer is $W \sim g_2/D = M_T g_1/D \propto \lambda(m \cdot g_1)$, where $M_T = (L+D)/L$ is the Talbot magnification [19,20]. Thus, a first way to decrease the angular width at a given wavelength is to increase the Talbot period. However, this rapidly increases the interferometer length, since the Talbot distance scales as the square of the period. Alternatively, one can increase the Talbot order m. However, since the width of the spectral region of high contrast scales as 1/m, this approach is also constrained by the use of a spectrally broad X-ray source, such as for instance a W anode tube.

Figure 14A:
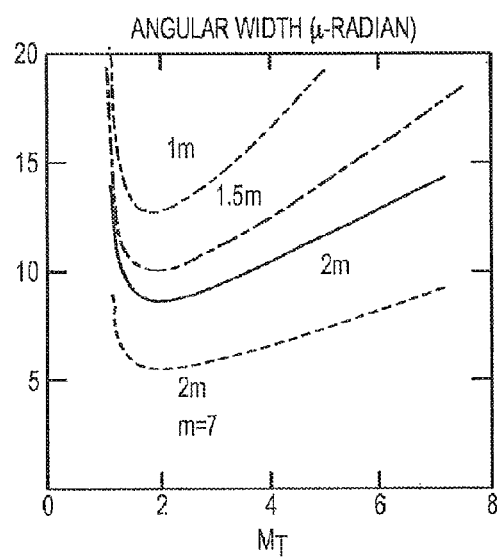
FIG. 14A shows dependence of angular width on interferometer length, for <E>=25 keV, m=3. Also shown the angular width for Z=2m and m=7 (dotted line).

The above relation shows that there are multiple combinations of grating period, Talbot order and distances that can be used for a given interferometer length, Z=L+D. To find the values that maximize the angular sensitivity for a given system length we plotted the Talbot interferometer equations as a function of the Talbot magnification $M_T = (L+D)/L$, with the mean energy <E>, Talbot order m and the system length Z, as parameters. The results for <E>=25 keV, m=3, and Z=1.0, 1.5, and 2 m are plotted in FIGS. 14A and 14B. R=5 cm was assumed in all cases. A first observation from FIG. 14A is that a small angular width requires a large interferometer length. A practical limit of a few m is however imposed for this length by mechanical stability considerations and by the photon flux available from conventional X-ray sources.

Figure 14B:
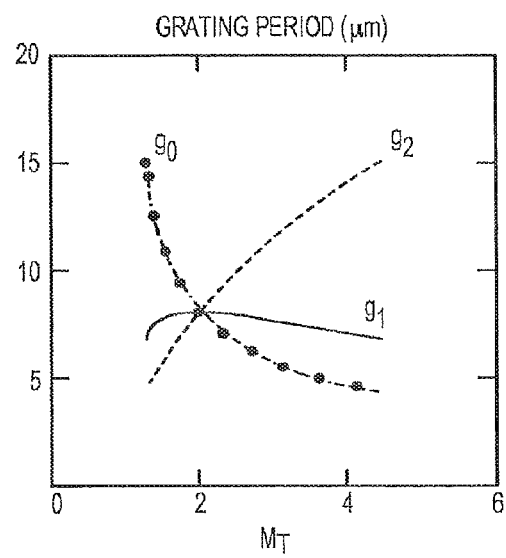
FIG. 14B shows grating period variation with $M_T$ for <E>=25 keV, Z=2m, m=3.

Secondly, FIG. 14A shows that for a given system length the angular width is minimized in a 'symmetrical' Talbot setup, having L=D ($M_T=2$). The dependence of the periods $g_0$, $g_1$ and $g_2$ on $M_T$ for Z=2 m and m=3 are shown in FIG. 14B, indicating that the symmetrical setup has also the practical advantage that all grating periods are equal and relatively large. For instance $g_0=g_1=g_2 \sim 8$ μm for $Z=2$ m, $E=25$ keV, $m=3$, which can be easily achieved in practice.

Thirdly, FIG. 14A shows that once the system length is fixed and the symmetrical setup chosen, the only way to further increase the angular sensitivity is to increase the Talbot order. However, as mentioned, when working with spectrally broad X-ray sources there is a limit to how much the angular sensitivity can be increased in this way, due to the decrease in spectrally averaged fringe contrast.

Figure 15:
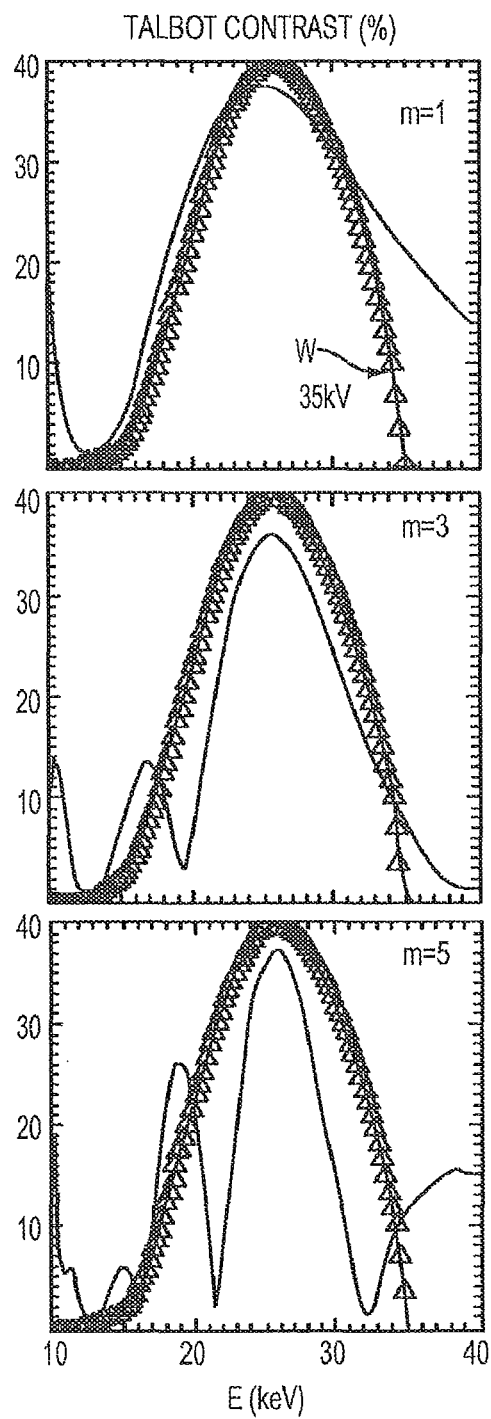
FIG. 15 shows computed contrast as a function of energy and Talbot order for 2 m interferometer of <E>=25 keV. Also shown the shape of the power spectrum of a W anode tube at 35 kV.

To illustrate this point, in FIG. 15 we plot the computed fringe contrast at increasing Talbot orders for a 2 m long symmetric interferometer having $<E>=25$ keV. We assumed 55 μm thick gold source and analyzer gratings and 33 μm thick Si phase grating. The source grating had openings of width $s_0=g_0/2$ (50% duty factor). The interferometer contrast is defined as above. The Talbot period was adjusted in each order to match the 2 m interferometer length. The contrast curves in FIG. 15 include also the geometrical broadening of the Talbot fringe pattern by the finite source grating openings, simulated by convolving the Talbot pattern at the analyzer with a Gaussian of width $s_0$ [20,21].

For comparison we also plotted in FIG. 15 the spectrum of a W anode X-ray tube at 35 kV, filtered with 1 mm Al and after traversing 20 mm of soft tissue. This approximates the spectrum incident on the beam-splitter for a small biomedical object such as the above joint phantom. As can be seen, the overlap between the contrast curve and the broad W anode spectrum rapidly decreases with increasing Talbot order. The spectrally averaged contrast is 32% for $m=1$, 27% for $m=3$, and 20% for $m=5$.

In conclusion, a practical configuration maximizing the angular sensitivity of the Talbot method is a symmetric setup having gratings of equal period and length of around 2 m. In addition, the third Talbot order offers a good compromise between angular sensitivity and contrast when using a spectrally broad source.

Nevertheless, as shown in FIG. 14A, the smallest angular width achievable with a Talbot interferometer in a low order ($m \leq 3$) is still several times larger than that of a crystal system. Thus, the only way to achieve with the Talbot method angular sensitivity closer to that of crystal optics is to use higher Talbot orders. For instance, as shown in FIG. 14A, nearly 5 μ-radian angular width can be obtained with a 2 m long interferometer in the 7th order.

Figure 16:
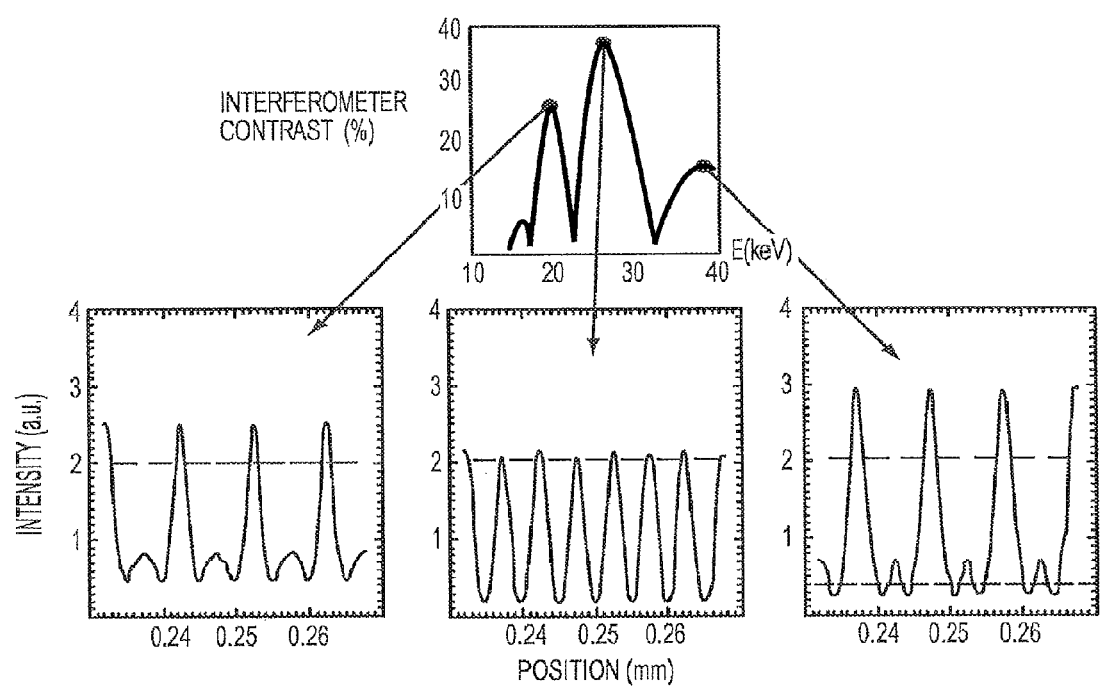
FIG. 16 shows computed Talbot pattern at the analyzer position for the m=5, E=<25 keV> interferometer in FIG. 15, at energies of 19, 25 and 37 keV. The position of the analyzer grating bars is shown by horizontal lines. For reference the m=5 contrast curve in FIG. 15 is also replotted at the top.

At the same time, as shown in FIG. 15, as the Talbot order is increased the interferometer contrast curve 'breaks' into m narrow peaks that have decreasing overlap with a broad source spectrum. Moreover, a detailed analysis shows that the higher order contrast curves in FIG. 15 are in a sense misleading, because the angular width changes with energy too. This is shown in FIG. 16 with plots of the computed Talbot pattern for the central (25 keV) and the adjacent (19 keV and 37 keV, respectively) $m=5$ contrast peaks in FIG. 15. As can be seen, among the $m=5$ peaks only that at the design energy of 25 keV has both high contrast and small angular width. The adjacent peaks are 'harmonics' that produce high contrast Talbot patterns, but having twice the period of the pattern of the central peak. As such, although a broad source spectrum would overlap with these side peaks, they would not contribute to the formation of the refraction image with the full angular sensitivity of the interferometer, but with half this value. In addition, depending on the details of the imaged object, these side peaks could subtract from the effective refraction contrast produced by the central peak, instead of adding to it.

In conclusion, our analysis shows that for interferometers of practical length the angular width of the Talbot method is intrinsically limited to values above 5 μ-radian approximately, which is higher than those of crystal systems (<1.5 μ-radian). In addition, to achieve its smallest possible angular width the Talbot interferometer must be operated in a high order, in which case it is not optimal to use a broad source spectrum, since the effective contrast substantially decreases.

The solution to simultaneously maximize the angular sensitivity and the effective contrast of Talbot method is thus to work in a high order ($m \geq 5$), while using a quasi-monochromatic X-ray spectrum of width $\Delta E/<E> \leq 1/m \sim 15-20\%$. Possible ways to do this are described in the following.

Talbot Interferometry with Quasi-Monochromatic Spectra

K-Line Spectra Filtered with K-Edge Absorbers.

The simplest method to obtain a quasi-monochromatic spectrum is to use a bright K-line emitter, such as a Mo or Rh anode tube for biomedical applications or an Ag K-α backlighter for HED plasma radiography, and to filter the emission with a K-edge absorber of the same atomic number as the emitter.

Figures 17A, 17B:
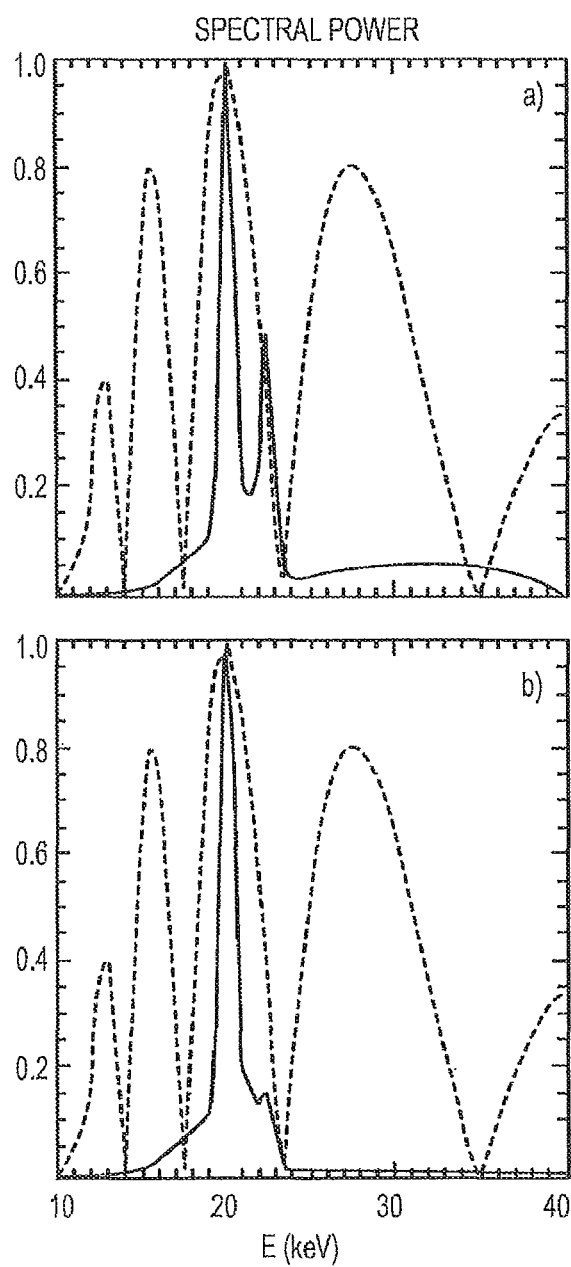
FIG. 17A shows a normalized power spectrum of Rh tube filtered with 30 μm Rh absorber; also shown the contrast of an m=7, <E>=20 keV symmetric interferometer.
FIG. 17B shows the spectrum corresponding to FIG. 17A after low-pass filtering by reflection on a Pt mirror at 3.5 mrad.

The spectrum of a Rh anode tube at 40 kVp filtered with 30 μm Rh absorber and after transmission through 20 mm of soft tissue is shown in FIG. 17A. Also shown in FIG. 17A is the computed contrast of a symmetric 2 m Talbot interferometer having 6 μm period, 55 μm thick Au source and analyzer gratings, $s_0=g_0/2$, Si phase grating optimized for 20 keV mean energy, and operated in the 7th order. As can be seen, the K-edge filtered spectrum is dominated by the strong Rh K-α line at 20 keV, which matches closely the peak of the contrast curve in the 7th order. A similar good match can be produced for the Mo K-α line at 17.5 keV.

The increase in refraction contrast possible using high Talbot orders and K-line/K-edge filtered spectra is illustrated with computed refraction enhanced images of the joint phantom in FIGS. 18A-18D. We assumed the above 2 m interferometer, a 50 μm pixel detector, and an exposure of 50 mA·s with a Rh anode tube at 40 kVp, producing a mean detector count of ~100 per pixel. The refraction enhanced images are computed for an interferometer phasing at mid-distance between the bright and dark field settings, which as illustrated in FIG. 11B maximizes the refraction contrast.

Figures 18A, 18B, 18C, 18D:
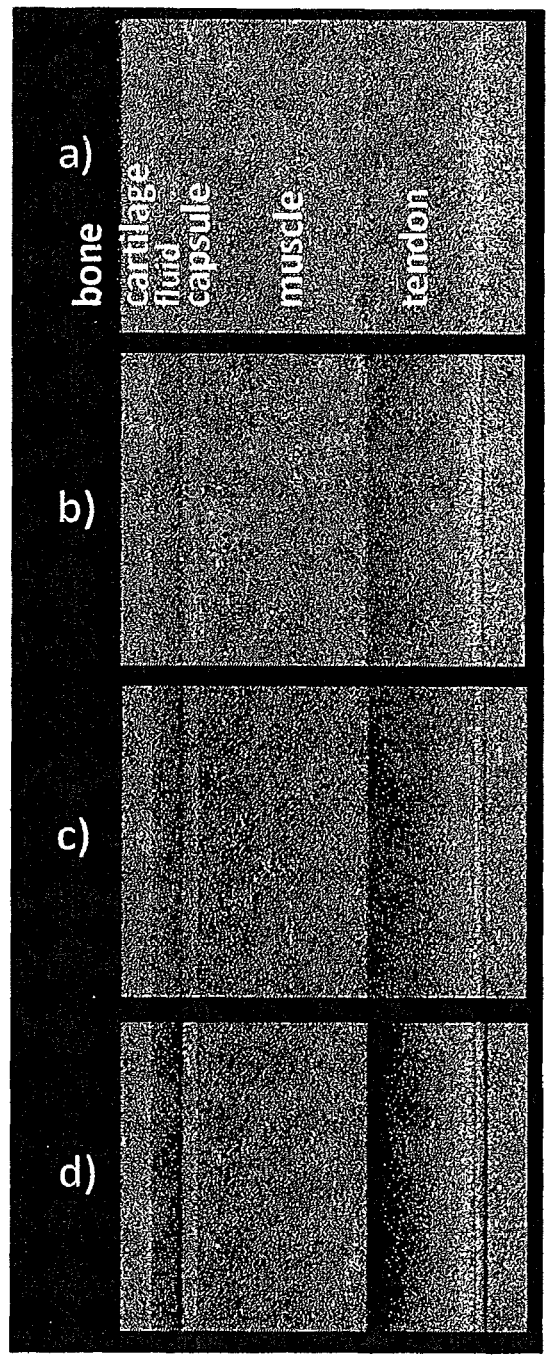
FIGS. 18A-18D show images of small joint phantom using different source spectra: a) W anode tube at 35 kV, m=3; b) K-edge filtered Rh tube spectrum at 40 kV, m=7; c) Total reflection mirror filtered Rh tube spectrum, m=7; and d) Multilayer mirror filtered Rh tube spectrum, m=7.

FIG. 18A shows as a reference the image obtained assuming the W anode tube spectrum in FIG. 15 and operation in the third Talbot order, optimal for this spectrum. As can be seen, due to insufficient angular sensitivity, the refraction contrast enhancement is too faint to be useful in practice without resorting to phase-scanning and/or CT, which would require multiple exposures.

FIG. 18B shows that the single exposure contrast can be substantially increased however by using the interferometer in the 7th order and the K-edge filtered Rh spectrum; the cartilage, joint fluid and connective capsule are clearly delineated in this case. The relative intensity variation or contrast at the cartilage fluid interface for instance is around 20%.

Figure 19:
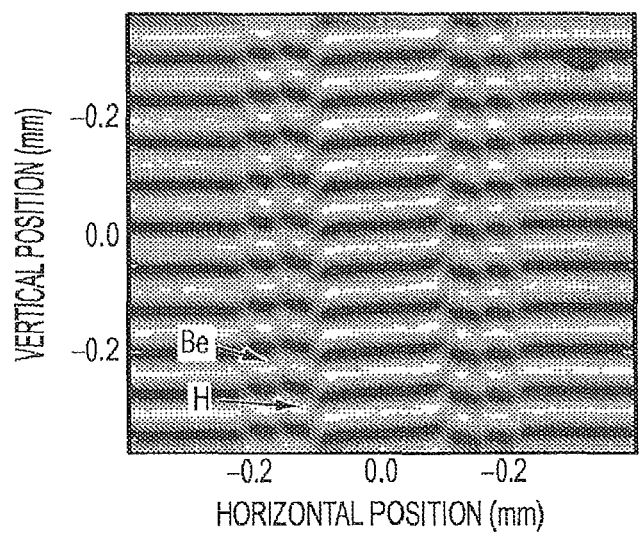
FIG. 19 shows a Moiré image of IFE capsule with Ag-Kα backlighting. The image of a 50 μm diameter opaque sphere is also shown in the top right corner as a contrast reference.

A HED plasma example of quasi-monochromatic imaging in a high Talbot order is illustrated in FIG. 19, which shows a Moiré fringe image or deflectogram of the IFE capsule modeled in FIG. 12. The use of Moiré deflectometry for density profile diagnostic in HED plasmas was demonstrated at the NOVA facility using backlighting with an XUV laser and focusing optics [29]. We assumed a symmetric interferometer of 4 m length and 10 μm period operated in the 5th Talbot order, a detector with 50 μm pixels, and illumination with a Ag K-α backlighter spectrum filtered with 50 μm Ag.

The clear Moiré fringe shifts at the location of the Be ablator and H fuel layer in FIG. 19 indicate that using the Talbot method with quasi-monochromatic backlighting would provide a simple density profile diagnostic for the capsule, without the need for X-ray lasers or focusing optics.

Mirror Filtered Slot-Scan Talbot Interferometers.

While offering the simplest approach, the contrast increase possible with K-edge filtering is limited, since as shown in FIG. 17A a substantial fraction of photons is emitted at energies above the K-α energy, where the interferometer has low angular sensitivity. In addition, the choice of bright K-line sources in the range of a few tens of keV is limited (e.g., only Mo or Rh anode tubes for medical applications).

To further increase the sensitivity and contrast of the Talbot method and to broaden the range of possible interferometer energies we propose to use X-ray mirrors or reflectors to shape the source spectrum. The principle of the method is sketched in FIG. 20. A grazing incidence mirror is placed near the source grating and a slot collimator selects only the reflected beam.

There are several choices for the filtering mirror. A first possibility is to use total reflection mirrors. These are simply made of a thin high-Z film (e.g., Au, Ta, Pt) deposited on a low-Z substrate and can reflect with high efficiency (>60-80%) hard X-rays incident below the critical reflection angle [30]. The sharp energy cutoff due to the total reflection effect can be used to efficiently filter out high energy photons. This is illustrated in FIG. 17B with the computed Rh tube spectrum at 40 kVp, filtered with a 30 μm Rh absorber followed by reflection on a Pt mirror at 3.5 mrad incidence angle. The mirror was assumed to have 3 Å surface roughness. As can be seen, the parasitic radiation above about 22 keV is completely suppressed, while the radiation in the useful Rh K-α band is efficiently transmitted.

The image of the joint phantom obtained assuming this spectrum is presented in FIG. 18C, showing that suppressing the parasitic band of high energy photons strongly increases the refraction contrast, with the intensity contrast at the cartilage fluid interface reaching ~35%. Another practical benefit of the mirror filtering technique is that it would allow increasing the brightness of the K-a band by increasing the tube voltage, since the photons above the K-α band are not reflected. It is advantageous to increase the K-α brightness by increasing the voltage rather than the current, since it scales as the voltage to the power of 1.5-1.6.

Another possibility with the mirror technique is to use laterally graded multilayer mirrors as narrow band, high throughput spectral filters. These are synthetic Bragg reflectors for which the period varies along the length, enabling it to reflect a narrow range of wavelengths over the entire length of a planar mirror [31]. Recent experiments demonstrate that at incidence angles of several milli-radians such mirrors can efficiently reflect X-rays up to tens of KeV. For instance, Park et al. demonstrated efficient production (≥50% reflectivity) of quasi-monochromatic X-ray bands using a conventional rotating anode X-ray tube and a 100 mm long graded multilayer with period varying between 32 and 38 Å [32]. The mean X-ray energy/bandwidth could be varied between 20 keV/15% and 40 KeV/7.5%. Curved HOPG (highly ordered pyrolytic graphite) reflectors could also be used to produce nearly monochromatic radiation from conventional X-ray sources, as demonstrated with a Mo K-α mammographic system by Lawaczeck et al. [33].

Using such reflectors, narrow K-α spectra can be produced that would further increase the refraction contrast of the Talbot method. This is illustrated in FIG. 18D assuming illumination of the joint phantom with photons in a 4 keV wide band centered on the Rh K-α energy. The contrast at the cartilage fluid interface reaches nearly 50% in this case. (Note that due to the narrower spectrum the K-α intensity in FIG. 18D was assumed to increase by a factor of ~3 to achieve the same photon count as in FIGS. 18B and 18C; as above discussed, this could be simply done by increasing the tube voltage from 40 to about 60 kV.)

The constraint in the mirror filtering method is that the field of view (FOV) height perpendicular to the mirror plane (vertical in FIG. 20) is limited to values H~Δα·d at the object location, with Δα the difference between the maximum and the minimum incidence angle on the mirror and d the distance between the mirror and the object. For total reflection mirrors Δα is constrained in turn by the acceptable variation in high energy cutoff across the length of the mirror. For instance, assuming a Rh anode spectrum at 60 kVp and a Pt mirror at 3.5 milli-radian central incidence angle, Δα of ~1 milli-radian would correspond to a cutoff energy variation between 22 keV and 28 keV, which would still allow obtaining high refraction contrast as in FIG. 18C. The vertical FOV at the object will thus be limited to H~1 mm for a 2 m long interferometer having d~L, as in FIG. 20. In the perpendicular direction the FOV is limited only by the available grating width, since large area X-ray mirrors can nowadays be easily produced.

With laterally graded multilayers the field of view height could be substantially larger, however, since the only limiting factor is the Bragg angle variation along the mirror. For instance, assuming the mirror parameters in Ref. 32, H would increase to ~2.5 mm for a 2 m long interferometer. Further on, using curved optics the field of view could be even larger; for instance, using a 50 mm long crystal with 480 mm curvature radius placed at 50 mm from the source Lawaczeck et al. achieved a 10 mm high FOV for Mo K-α radiation, at 550 mm distance from the source [33]. For a 2 m long symmetric Talbot interferometer this would translate into a FOV height of ~15 mm.

Figure 20:
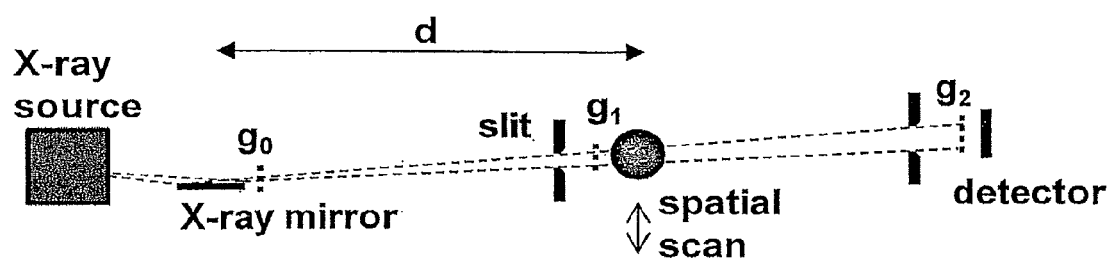
FIG. 20 is a schematic illustration of a differential phase contrast X-ray imaging system according to an embodiment of the current invention.

Nonetheless, to image large objects, the mirror filtered Talbot interferometer would need to work in a slot-scan mode, in which either the object or the interferometer field of view is scanned vertically in FIG. 20. This would require, in principle, longer measurement times than possible with a large field of view, 'cone-beam' system. We note however that a compensating advantage of the slot-scan geometry could be the strong reduction in large angle scattered radiation reaching the detector. As demonstrated by slot-scan medical systems this reduction substantially improves the overall image contrast [32-34]. In addition, using a quasi-monochromatic spectrum has the advantage of decreasing the radiation dose, since only the wavelength useful for imaging is incident on the object [33,34]. The slot-scan Talbot systems would also closer resemble the crystal ABI systems, which as above discussed also reject the large angle scattered radiation. Lastly, the measurement time of a mirror filtered slot-scan system could be drastically shortened by using multiple, stacked reflectors. This was demonstrated by Park et al., who used an array of stacked multilayer mirrors to achieve scan times of less than 1 s for an image of ~200 mm×240 mm size [32].

The mirror filtering could enable also extending the range of energy bands available for quasi-monochromatic Talbot interferometry. This could be done using narrow band-pass mirrors in combination with a bright continuum source, such as a rotating W anode tube. A first way to obtain narrow energy bands could be to use depth graded multilayer mirrors. These are multilayers for which the period varies with the depth, enabling to efficiently produce energy bands of width ΔE/<E>~10-15%, for X-rays up to several tens of keV energy [35,36].

Figure 3B:
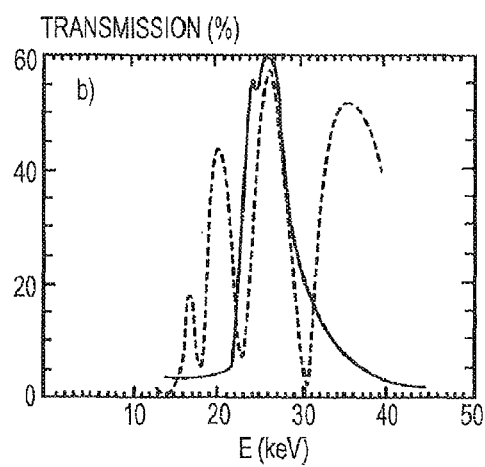
FIG. 3B shows computed optical transmission of a dual-mirror filter (FIG. 3A) obtained combining two Pt mirrors at 3 mrad incidence angle, of which the first is deposited on a 3 μm thick Mylar membrane. Also shown the shape of the contrast curve of an m=5, <E>=26 keV Talbot interferometer.

In addition, a simple and tunable band-pass filter could be made using two total reflection mirrors. This dual-mirror filter design is sketched in FIG. 3A and expands on a filtering technique demonstrated at the synchrotrons (the 'transmission mirror') [37,38]. The first mirror has a high-Z metallic film deposited on a thin (few μm) low-Z membrane. Total reflection on this mirror rejects the low energy part of the spectrum, while the high energy part is transmitted through the thin membrane with little attenuation. The radiation transmitted by the first mirror is then low-pass filtered by a second total reflection mirror. FIG. 3B shows an example of the spectral response possible with this design, indicating that band-pass of the order of 15-20% could be achieved for energies of up to several tens of keV. These energy bands would in turn match well the contrast of Talbot interferometers in high orders, as also illustrated in FIG. 3B.

Lastly, a further improvement to the mirror filtered interferometer design would be to combine the source grating and the filter mirror in a single optical element, using the micro-periodic mirror concept we described in Ref. 30. These are total reflection 'mirror gratings' made by patterning a low-Z substrate with thin (~500 Å), periodic strips of high-Z metal. As shown in Ref. 30, the difference in reflectivity between the high-Z strips and the low-Z substrate enables one to produce high contrast (up to ~80%) reflection gratings for X-ray energies up to several tens of keV. Thus, in addition to simplifying the optical setup, the use of a micro-periodic mirror instead of the 'source' grating would allow increasing the interferometer contrast at high energy, since the mirror would be the equivalent a very thick absorption grating.

Figures 21A, 21B:
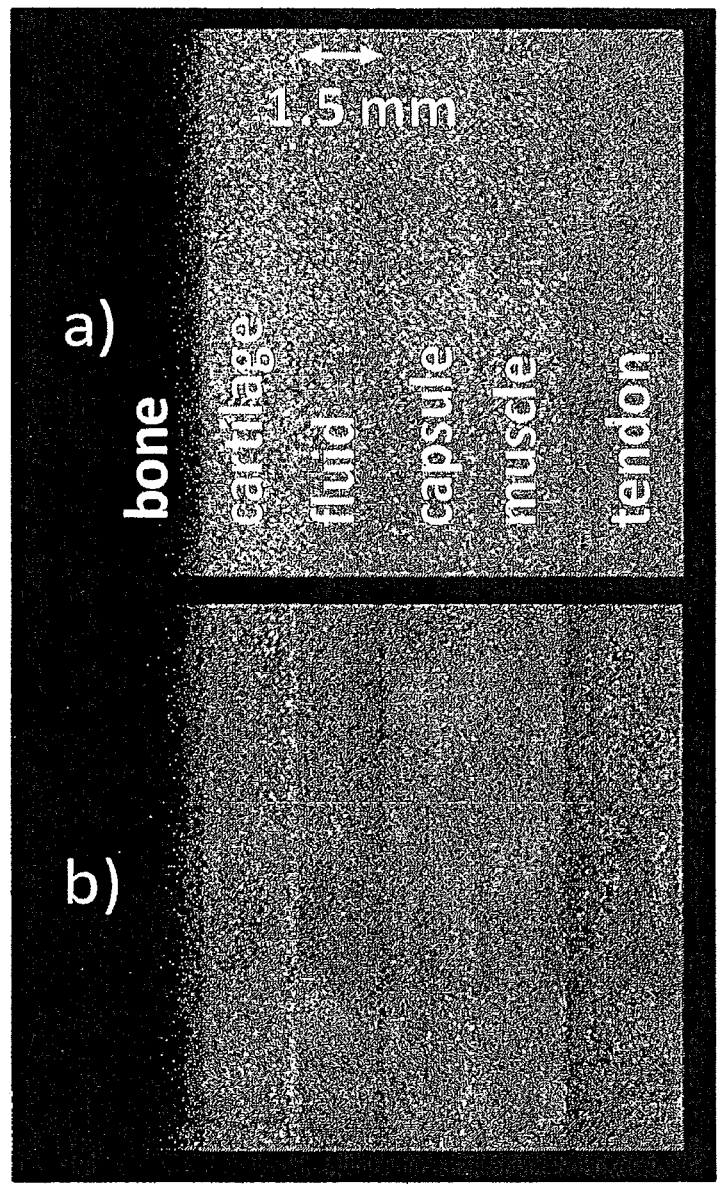
FIG. 21A shows a computed refraction enhanced image of large joint phantom using separate, absorption source grating and mirror filtering.
FIG. 21B shows a phantom image obtained assuming a micro-periodic mirror as reflective source grating.

This possibility is illustrated in FIGS. 21A-21B with calculations of refraction enhanced images for a large joint phantom. The phantom has the same layout as the one in FIG. 13, but with dimensions typical of a knee joint (15 cm muscle diameter, 1.5 mm thick cartilage, fluid and connective tissue layers, 35 mm bone diameter and 6 mm diameter tendon). As the source, we assumed a W anode tube of 0.3 mm spot operated at 70 kVp (typical of knee radiography) and filtered with 0.12 mm Cu and 2 mm Al. The detector had 100 μm pixels.

FIG. 21A shows the image obtained assuming a 2.2 m long symmetric interferometer of 45 keV mean energy and 5 μm period, operated in the 5th order, and using 100 μm thick source and analyzer gratings, with a source grating duty factor of 33%. The photons above ~50 keV are cut by a Pt mirror at 1.8 milli-radian incidence angle. As can be seen, the refraction contrast for soft tissues is poor because the absorption contrast between the bars and the openings of the source grating decreases rapidly for X-rays above a few tens of keV.

FIG. 21B shows the image obtained assuming instead of the source grating a micro-periodic Pt mirror, having 33% duty factor and 80% reflection contrast between the reflecting and non-reflecting strips, independent of energy [30]. As can be seen, replacing the grating with a micro-periodic mirror would strongly improve the refraction contrast at high energy, making visible all soft tissues in the large joint. Lastly, to achieve the maximum possible refraction contrast the source grating could be replaced with a micro-periodically patterned multilayer mirror or possibly a patterned HOPG crystal, for near monochromatic differential phase-contrast imaging at high energy.

CONCLUSIONS

Our analysis shows that while Talbot interferometry is a simple technique for refraction based imaging, its angular sensitivity and contrast should be carefully optimized in order to compete with those of the crystal method. This is particularly critical for demanding applications such as soft tissue imaging or high energy density plasma diagnostic, where the refraction angles can be in the sub μ-radian range. A practical way to simultaneously maximize the angular sensitivity and contrast of the Talbot method is to use a symmetric interferometer setup with a quasi-monochromatic source spectrum. Several solutions are described for shaping the source spectrum, ranging from K-edge absorption filters to reflection on grazing incidence mirrors. The calculations suggest that using such filtering strong refraction contrast could be obtained for low-Z objects at energies up to a few tens of keV. The combination of Talbot gratings with band-pass mirrors and/or micro-periodic mirrors appears also attractive for extending the Talbot method to higher X-ray energy.

REFERENCES

1. S.-A. Zhou and A. Brahme, *Physica Medica* 24 129 (2008)
2. Keyriläien J, Bravin A, Fernandez M, Tenhunen M, Virkkunen P and Suortti P, *Acta Radiologica* 8 866(2010)
3. D Chapman, W Thomlinson, R E Johnston, D Washburn, E Pisano, N Gmür, Z Zhong, R Menk, F Arfelli and D Sayers *Phys. Med. Biol.* 42 2015(1997)
4. Carol Muehleman, Jun Li, Zhong Zhong, J ovan G Brankov, and Miles N Wernick, J Anat. 2006 208, 115-124
5. Suhonen H., Fernandez M., Bravin A., Keyrilainen J. and Suorttia P., *J. Synchrotron Rad.* 14, 512 (2007)
6. Arfelli F., Rigon L. and Menk R. H., *Phys. Med. Biol.* 55 1643(2010)
7. R. A. Lewis, *Phys. Med. Biol.* 49 3573(2004)
8. A. W. Stevenson, T. E. Gureyev, D. Paganin, S. W. Wilkins, T. Weitkamp, A. Snigirev, C. Rau, I. Snigireva, H. S. Youn, I. P. Dolbnya, W. Yun, B. Lai, R. F. Garrett, D. J. Cookson, K. Hyodo, M. Ando, *Nuclear Instruments and Methods in Physics Research* B 199 427(2003)
9. S. Mayo, R. Evans, F. Chen and R. Lagerstrom, *Journal of Physics: Conference Series* 186, 012105 (2009)
10. Brey E M, Appel A, Chiu Y C, Zhong Z, Cheng M H, Engel H, Anastasio M A, *Tissue Eng. Part C Methods.* 16, 1597 (2010)
11. Jeffrey A. Koch, Otto L. Landen, Bernard J. Koziziemski, Nobuhiko Izumi, Eduard L. Dewald, Jay D. Salmonson, and Bruce A. Hammel, *J. Appl. Phys.* 105, 113112 (2009)
12. D. Stutman, M. Finkenthal and N. Moldovan, *Rev. Sci. Instrum.* 81, 10E504 (2010)
13. Momose A, Yashiro W, Takeda Y, Suzuki Y and Hattori T, *Japanese Journal of Applied Physics* 45 5254 (2006)
14. Pfeiffer F, Weitkamp T, Bunk O and David C, *Nature Physics* 2, 258 (2006)
15. Pfeiffer F, Bech M, Bunk O, Kraft P, Eikenberry E F, Bronnimann Ch, Grunzweig C and David C, *Nature Materials* 7, 134 (2008)
16. Bech M, H Jensen T H, Feidenhans R, Bunk O, David C and Pfeiffer F, *Phys. Med. Biol.* 54 2747 (2009)

17. Donath T, Pfeiffer F, Bunk O, Grünzweig C, Eckhard H, Popescu S, Peter V and David C, *Investigative Radiology* 45, 445 (2010)
18. Shimao D, Kunisada T, Sugiyama H, Ando M, *European Journal of Radiology* 68 S27(2008)
19. Donath T, Chabior M, Pfeiffer F, *J. Appl. Phys.* 106 054703(2009)
20. Weitkamp T, David C, Kottier C, Bunk O and Pfeiffer F, *Proc. SPIE* vol 6318, Developments in X-Ray Tomography V, 28 (2006)
21. Engelhardt M, Kottler C, Bunk O, David C, Schroer C, Baumann J, Schuster M, Pfeiffer F., *Journal of Microscopy* 232, 145 (2008)
22. David C, Bruder J, Rohbeck T, Grunzweig C, Kottler C, Diaz A, Bunk O and Pfeiffer F, *Microelectronic Engineering* 84, 1172(2007)
23. Reznikova E, Mohr J, Boerner M, Nazmov V, Jakobs P-J, *Microsyst. Technol.* 14 1683(2008)
24. Weitkamp T, *Proc. SPIE* vol 5536 Advances in Computational Methods for X-Ray and Neutron Optics, 181 (2004)
25. Sanchez del Rio M and Dejus R J, *Proc. SPIE* vol 3448 Crystal and Multilayer Optics, 340(1998)
26. H.-S. Park, B. R. Maddox, E. Giraldez, et al., Physics of Plasmas 15, 07270(2008)
27. R. Tommasini, LLNL Report, LLNL-TR-429373, 2010
28. Woodard H Q and White D R, *The British Journal of Radiology* 59, 1209(1986)
29. D. Ress, L. B. DaSilva, R. A. London, J. E. Trebes, and R. A. Lerche, *Rev. Sci. Instrum.* 66, 579 (1995)
30. D. Stutman, M. Finkenthal, N. Moldovan, *Applied Optics* 49, 4677(2010)
31. M. Schuster, H. Göbel, L. Brugemann, D. Bahr, F. Burgazy, C. Michaelsen, C. M. Störmer, C P. Ricardo, C R. Dietsch, T. Holz and H. Mai, *Proc. SPIE* vol 3767 EUV, X-Ray, and Neutron Optics and Sources, 183 (1999)
32. Y. Park, S. Han, J. Chae, C. Kim, K. S. Chon, H.-K. Lee and D. S. Han, *Proc. SPIE* 7258 Medical Imaging 2009: Physics of Medical Imaging, 72583L (2009)
33. R. Lawaczeck, V. Arkadiev, F. Diekmann, and M. Krumrey, *Investigative Radiology* 40, 33 (2005)
34. K Hussein, C L Vaughan and T S Douglas, *Phys. Med. Biol.* 54 1533(2009)
35. K. D. Joensen, P. Høghøj, F. Christensen, P. Gorenstein, J. Susini, E. Ziegler, A. Freund, J. Wood, *Proc. SPIE* vol 2011 Multilayer and Grazing Incidence X-Ray/EUV Optics II, 360(1994)
36. A. Rack, T. Weitkamp, M. Riotte, T. Rack, R. Dietsch, T. Holz, M. Krämer, F. Siewert, M. Meduna, Ch. Morawe, P. Cloetens, E. Ziegler, *Proc. SPIE* Vol. 7802, Advances in X-Ray/EUV Optics and Components V, 78020M-1 (2010)
37. S. Cornaby and D. H. Bilderback, *J. Synchrotron Rad.* 15, 371 (2008)
38. A. Iida, T. Matsushita, and Y. Gohshi, *Nucl. Instrum. Meth. Phys. Res.* A235, 597(1985)

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:
1. A method for X-ray illumination, comprising:
   providing a poly-energetic X-ray beam for illuminating an object to be imaged;
   reflecting a first portion of said poly-energetic X-ray beam, the first portion comprising X-rays that have energies less than a lower pass-band energy;
   transmitting a second portion of said poly-energetic X-ray beam
   attenuating said first portion of said poly-energetic X-ray beam;
   reflecting a third portion of said second portion of said poly-energetic X-ray beam, said third portion comprising X-rays that have energies less than an upper pass-band energy;
   attenuating a fourth portion of said second portion of said poly-energetic X-ray beam, the fourth portion comprising X-rays that are not reflected; and
   providing said third portion of said second portion of said poly-energetic X-ray beam to illuminate said object to be imaged, wherein said third portion comprises X-rays having energies between said upper pass-band energy and said lower pass-band energy.
2. The method according to claim 1, wherein said reflecting said first portion of said poly-energetic X-ray beam and said transmitting said second portion of said poly-energetic X-ray beam further comprises:
   directing said poly-energetic X-ray beam to be incident upon a membrane X-ray mirror comprising a reflecting layer that comprises a high-Z material on a support layer that comprises a low-Z material,
   wherein Z is an atomic number,
   wherein said high-Z material includes atomic elements with Z at least 42, and
   wherein said low-Z material includes atomic elements with Z less than 14.
3. The method according to claim 1, wherein said reflecting said first portion of said poly-energetic X-ray beam and said transmitting said second portion of said poly-energetic X-ray beam further comprises:
   directing said poly-energetic X-ray beam to be incident upon a membrane X-ray mirror comprising a reflecting layer that comprises a first material on a support layer that comprises a second material.
4. The method according to claim 3,
   wherein said first material is a high-Z material,
   wherein Z is an atomic number,
   wherein said high-Z material includes atomic elements with Z at least 42.
5. The method according to claim 3, wherein said first material is at least one of Rh, Pt, or Au.
6. The method according to claim 3,
   wherein said second material is a low-Z material,
   wherein Z is an atomic number,
   wherein said low-Z material includes atomic elements with Z less than 14.
7. The method according to claim 3, wherein said second material is at least one of C, Si, quartz, or glass.

\* \* \* \* \*